United States Patent
Reboud et al.

(10) Patent No.: US 11,771,846 B2
(45) Date of Patent: *Oct. 3, 2023

(54) NEBULISATION OF LIQUIDS

(71) Applicant: The University Court of the University of Glasgow, Glasgow (GB)

(72) Inventors: Julien Reboud, Glasgow (GB); Robert Wilson, Glasgow (GB); Jonathan Cooper, Glasgow (GB)

(73) Assignee: The University Court of the University of Glasgow, Glasgow (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/711,748

(22) Filed: Apr. 1, 2022

(65) Prior Publication Data

US 2022/0288329 A1   Sep. 15, 2022

Related U.S. Application Data

(63) Continuation of application No. 15/525,509, filed as application No. PCT/EP2015/076359 on Nov. 11, 2015, now Pat. No. 11,311,686.

(30) Foreign Application Priority Data

Nov. 11, 2014 (GB) .................................. 1420061

(51) Int. Cl.
*A61M 11/00* (2006.01)
*A61M 15/00* (2006.01)
(Continued)

(52) U.S. Cl.
CPC ...... *A61M 11/005* (2013.01); *A61M 15/0085* (2013.01); *B05B 17/0607* (2013.01);
(Continued)

(58) Field of Classification Search
CPC .............. A61M 11/005; A61M 11/001; A61M 15/001; A61M 15/0085;
(Continued)

(56) References Cited

U.S. PATENT DOCUMENTS 4,336,514 A   6/1982 Paige
5,455,178 A   10/1995 Fattinger
(Continued)

FOREIGN PATENT DOCUMENTS

CN   1455985      11/2003
CN   2744401 Y    12/2005
(Continued)

OTHER PUBLICATIONS

English Machine Translation of JP-2012148256-A provided by Espacenet (Year: 2012).*
(Continued)

*Primary Examiner* — Joseph D. Boecker
*Assistant Examiner* — Brian T Khong
(74) *Attorney, Agent, or Firm* — Rudy J. Ng; Bozicevic, Field & Francis LLP

(57) ABSTRACT

A device is disclosed for the preparation of nebulised droplets, for inhalation. The device has: a surface acoustic wave (SAW) transmission surface; a SAW transducer adapted to generate and propagate SAWs along the SAW transmission surface; and an array of cavities opening at the SAW transmission surface for containing a liquid. In operation, SAWs propagating along the SAW transmission surface interact with the liquid in the cavities to produce nebulised droplets of the liquid. Operation of the device results in a nebulised plume of droplets of average diameter in the range 1-5 μm.

19 Claims, 9 Drawing Sheets

(51) Int. Cl.
  *B05B 17/06* (2006.01)
  *H03H 9/145* (2006.01)
(52) U.S. Cl.
  CPC ............ *A61M 2202/0468* (2013.01); *A61M 2205/0238* (2013.01); *A61M 2205/0294* (2013.01); *H03H 9/14502* (2013.01)
(58) Field of Classification Search
  CPC ....... A61M 2205/0294; B05B 17/0607; B05B 17/06; B05B 17/0615; B05B 17/0638; B05B 17/0646; B05B 17/0669; B05B 17/0661; Y02B 30/80; A61K 41/0014; H03H 9/14502; H03H 9/145
  See application file for complete search history.

(56) References Cited

U.S. PATENT DOCUMENTS

| | | | |
|---|---|---|---|
| 5,586,550 A * | 12/1996 | Ivri | A61M 11/005 128/200.14 |
| 5,906,549 A | 5/1999 | Kubica | |
| 5,996,903 A | 12/1999 | Asai et al. | |
| 6,210,128 B1 | 4/2001 | Rife et al. | |
| 6,362,543 B1 | 5/2002 | Ellis | |
| 6,459,080 B1 | 10/2002 | Yin et al. | |
| 6,565,052 B1 | 5/2003 | Rife et al. | |
| 6,603,118 B2 | 8/2003 | Ellson et al. | |
| 6,707,038 B2 | 3/2004 | Ellson et al. | |
| 6,710,335 B2 | 3/2004 | Ellson et al. | |
| 6,739,531 B2 | 5/2004 | Taylor | |
| 6,777,245 B2 | 8/2004 | Wixforth | |
| 6,809,315 B2 | 10/2004 | Ellson et al. | |
| 6,855,925 B2 | 2/2005 | Ellson et al. | |
| 7,103,949 B2 | 9/2006 | Rife et al. | |
| 7,172,897 B2 | 2/2007 | Blackburn et al. | |
| 7,405,395 B2 | 7/2008 | Ellson et al. | |
| 7,459,304 B2 | 12/2008 | Gauer | |
| 7,731,412 B2 | 6/2010 | Sparey-Taylor et al. | |
| 7,880,563 B2 | 1/2011 | Khelif et al. | |
| 7,942,568 B1 | 5/2011 | Branch et al. | |
| 8,415,619 B2 | 4/2013 | Goodlett et al. | |
| 2001/0055529 A1 | 12/2001 | Wixforth | |
| 2002/0037579 A1 | 3/2002 | Ellson | |
| 2003/0085952 A1* | 5/2003 | Williams | B41J 2/14008 347/46 |
| 2003/0175947 A1 | 9/2003 | Liu et al. | |
| 2004/0042915 A1 | 3/2004 | Rife et al. | |
| 2004/0101975 A1 | 5/2004 | Gauer | |
| 2004/0115097 A1 | 7/2004 | Wixforth et al. | |
| 2004/0257906 A1 | 12/2004 | Scriba et al. | |
| 2006/0060769 A1 | 3/2006 | Bousse et al. | |
| 2007/0128046 A1 | 6/2007 | Gonnella et al. | |
| 2007/0140041 A1 | 6/2007 | Sparey-Taylor et al. | |
| 2007/0252083 A1 | 11/2007 | Arscott et al. | |
| 2007/0264161 A1 | 11/2007 | Rathgeber | |
| 2008/0094937 A1 | 4/2008 | Li et al. | |
| 2008/0211602 A1 | 9/2008 | Khelif et al. | |
| 2009/0098027 A1 | 4/2009 | Tabata et al. | |
| 2009/0242663 A1 | 10/2009 | Yu | |
| 2010/0139377 A1 | 6/2010 | Huang et al. | |
| 2010/0191277 A1 | 7/2010 | McEwen et al. | |
| 2010/0200092 A1 | 8/2010 | Beltram et al. | |
| 2010/0206696 A1 | 8/2010 | Kondoh | |
| 2010/0324417 A1 | 12/2010 | McNair | |
| 2011/0068193 A1 | 5/2011 | Machi et al. | |
| 2012/0035081 A1 | 2/2012 | Lin | |
| 2012/0145890 A1 | 6/2012 | Goodlett et al. | |
| 2012/0149126 A1 | 6/2012 | Wilson et al. | |
| 2012/0187209 A1* | 7/2012 | Friend | A61P 11/00 239/4 |
| 2013/0079733 A1 | 3/2013 | Burt | |
| 2013/0186975 A1 | 7/2013 | Hogan | |
| 2013/0213488 A1 | 8/2013 | Weitz et al. | |
| 2013/0330247 A1 | 12/2013 | Wilson et al. | |
| 2013/0334339 A1 | 12/2013 | Xu | |
| 2014/0083174 A1 | 3/2014 | Reboud et al. | |
| 2017/0280771 A1 | 10/2017 | Courbat et al. | |
| 2018/0036498 A1 | 2/2018 | Atkinson et al. | |

FOREIGN PATENT DOCUMENTS

| | | | |
|---|---|---|---|
| CN | 101301990 | 11/2008 | |
| CN | 102985190 | 3/2013 | |
| EP | 1366356 | 7/2010 | |
| EP | 2338609 | 4/2014 | |
| EP | 2500106 | 9/2017 | |
| EP | 3017876 | 11/2019 | |
| JP | 11114467 | 4/1999 | |
| JP | 2008104966 | 5/2008 | |
| JP | 2012143726 | 8/2012 | |
| JP | 2012148256 A * | 8/2012 | ............. B05B 17/06 |
| WO | WO 01504813 | 8/2001 | |
| WO | WO 01070381 | 9/2001 | |
| WO | WO 00062931 | 11/2001 | |
| WO | WO 2002071051 | 9/2002 | |
| WO | WO 2003055976 | 7/2003 | |
| WO | WO 2004085079 | 10/2004 | |
| WO | WO 2005100953 | 10/2005 | |
| WO | WO 2006087496 | 8/2006 | |
| WO | WO 2007070957 | 6/2007 | |
| WO | WO 2007118224 | 10/2007 | |
| WO | WO 2007128045 | 11/2007 | |
| WO | WO 2007128046 | 11/2007 | |
| WO | WO 2007132211 | 11/2007 | |
| WO | WO 2008040008 | 4/2008 | |
| WO | WO 2008089174 | 10/2008 | |
| WO | WO 2009073402 | 6/2009 | |
| WO | WO 2009122340 | 10/2009 | |
| WO | WO 2010129994 A1 | 11/2010 | |
| WO | WO 2012096378 | 1/2011 | |
| WO | WO 2011023949 | 3/2011 | |
| WO | WO 2011060369 | 5/2011 | |
| WO | WO 2012097378 | 7/2012 | |
| WO | WO 2012099291 | 7/2012 | |
| WO | WO 2012114076 | 8/2012 | |
| WO | WO-2012114076 A1 * | 8/2012 | ........ B01L 3/502707 |
| WO | WO 2012156755 | 11/2012 | |
| WO | WO 2013166542 | 11/2013 | |
| WO | WO 2014132228 A1 | 9/2014 | |
| WO | WO 2016179664 | 11/2016 | |

OTHER PUBLICATIONS

Ehlers et al., (1996) "Do cyanobacteria swim using traveling surface waves?," Proc Natl Acad Sci 93: 8340-8343.
Ennis et al., (2011) "Current status of the use of modalities in wound care: electrical stimulation and ultrasound therapy," Plast Reconstr Surg. 127(Suppl 1):93-102.
Eschbach et al. (2001) "Improved Erythrocyte Lysis Assay in Microtitre Plates for Sensitive Detection and Efficient Measurement of Haemolytic Compounds from Ichthyotoxic Algae," J. Appl. Toxicol., 21, 513-519.
Franke et al., (2010) "Surface acoustic wave actuated cell sorting (SAWACS)," Lab Chip, 10, 789-794.
Friend and Yeo (2011) "Microscale acoustofluidics: Microfluidics driven via acoustics and Ultrasonics," Rev Mod Phys 83(2): 647-704.
Frommelt et al., (2008) "Flow patterns and transport in Rayleigh surface acoustic wave streaming: combined finite element method and raytracing numerics versus experiments," Ultrasonics, Ferroelectrics and Frequency Control, IEEE Transactions on, 55(10), 2298-2305.
Fu et al (2010) "Recent developments on ZnO films for acoustic wave bio-sensing and microfluidics applications: a review" Sensors and Actuators B: Chemical,143: 606-619.
Guenneau et al., (2007) "Acoustic metamaterials for sound focusing and confinement," New J. Phys. 9:1-18.
Guttenberg et al., (2005) "Planar chip device for PCR and hybridization with surface acoustic wave pump," Lab Chip 5:308-317.

(56) References Cited

OTHER PUBLICATIONS

Hall et al., (2007) "A Real-Time Measure of Cavitation Induced Tissue Disruption by Ultrasound Imaging Backscatter Reduction," IEEE transactions on ultrasonics, ferroelectrics, and frequency control, 54 (3): 569-575.
Heron et al., (2010) "Surface Acoustic Wave Nebulization of Peptides As a Microfluidic Interface for Mass Spectrometry," Anal. Chem. 82, 3985-3989.
Ho et al., (2011) "Paper-based microfluidic surface acoustic wave sample delivery and ionization source for rapid and sensitive ambient mass spectrometry" Anal. Chem. 83(9):3260-3267.
Hodgson et al. (2009) "Transmitting high power rf acoustic radiation via fluid couplants into superstrates for microfluidics," Appl. Phys. Lett., 94, 024102-024103.
Hsu and Wu (2006) "Efficient formulation for band-structure calculations of two dimensional phononic-crystal plates," Phys Rev. B, 74, 144303-1-144303-7.
Kim et al., (2005) "A device for fabricating protein chips by using a surface acoustic wave atomizer and electrostatic deposition," Sensors and Actuators B, 107: 535-545.
Kondoh et al.(2009) "Development of temperature-control system for liquid droplet using surface acoustic wave devices," Sensors and Actuators A, 149: 292-297.
Kondoh et al., (2005) "Liquid Heating Effects by SAW Streaming on the Piezoelectric Substrate," IEEE transactions an ultrasonics, ferroelectrics, and frequency control, 52 (10): 1881-1883.
Kuo et al., (2009) "Demonstration of inverse acoustic band gap structures in AlN and integration with piezoelectric contour mode wideband transducers," Joint Meeting of the European Frequency and Time Forum and the IEEE International Frequency Control Symposium (EFTF-IFCS 2009) 2334-2337.
Kuo and Ye (2004) "Sonic crystal lenses that obey the lensmaker's formula," Journal of Physics D—Applied Physics, 37: 2155-2159.
Kurosawa et al., (1995) "Surface acoustic wave atomizer," Sensors and Actuators A, 50: 69-74.
Kurosawa et al., (1996) "Ultrasonic linear motor using surface acoustic waves," IEEE Trans Ultrason Ferroelectr Freq Control 43(5): 901-906.
Laude et al., (2005) "Full band gaps for surface acousticwaves in piezoelectric phononic crystals," Physical Review E Ultrasonics Symposium 71: 036607-7.
Lee and Cho (2007) "A continuous electrical cell lysis device using a low dc voltage for a cell transport and rupture," Sensors and Actuators B, 124: 84-89.
Li et al., (2007) "Surface acoustic wave concentration of particle and bioparticle suspensions," Biomedical Microdevices, 9:647-656.
Lighthill, (1978) "Acoustic streaming," J. Sound Vib., 61(3): 391-418.
Miyagawa et al. (1997) "Development of ultra-small sized servo actuator with brushless DC motor, planetary gear drive and optical rotary encoder," International Journal of the Japan Society for Precision Engineering 63(8): 1073-1076. [Note that this document is primarily in the Japanese language. However, its disclosure can be understood based on the English title, the keywords, drawings and images.].
Mohammadi, et al., (2007) "Complete phononic bandgaps and bandgap maps in two-dimensional silicon phononic crystal plates," Electronics Letters, 43(16): 898-899.
Mohammadi et al., (2008) "Evidence of large high frequency complete phononic band gaps in silicon phononic crystal plates," Applied Physics Letters, 92(22): 221905-3.
Moroney et al., (1991) "Microtransport induced by ultrasonic Lamb waves," Appl. Phys. Lett., 59: 774-776.
Morton et al.,(2008) "Hydrodynamic metamaterials: Microfabricated arrays to stee, refract, and focus streams of biomaterials," PNAS, 105(21): 7434-7438.
Muller et al., (2007) "Surface acoustic wave devices," Zinc Oxide Materials and Devices II 6474:647413-647415.
Neuzil et al., (2006) "Disposable real-time microPCR device: lab-on-a-chip at a low cost," Mol. BioSyst., 2: 292-298.

Nyborg (1965) "Acoustic Streaming," Academic Press, New York, 265-331.
Olsson et al., (2008) "Microfabricated VHF acoustic crystals and waveguides" Sensors and Actuators a—Physical, 145-146: 87-93.
Pál et al. (2009) "Hybrid ZnO/polymer thin films prepared by RF magnetron sputtering," Colloid and Polymer Science, 287(4): 481-485.
Pennec et al. (2005) "Acoustic channel drop tunneling in a phononic crystal," Appl. Phys. Lett. 87:261912-261913.
Prada et al., (2009) "Influence of the anisotropy on zerogroup velocity Lamb modes," J. Acoust. Soc. Am. 126(2):620-625.
Qi et al. (2009) "Miniature inhalation therapy platform using surface acoustic wave microfluidic atomization," Lab on Chip, 9, 2184 2193.
Qiu et al., (2005) "Mode-selecting acoustic filter by using resonant tunnelling of two-dimensional double phononic crystals," Appl. Phys. Lett. 87:104101-104103.
Raghaven et al., (2010) "Particle concentration via acoustically driven microcentrifugation: microPIV flow visualization and numerical modelling studies," Micorfluid. Nanofluid, (8):73-84.
Renaudin et al., (2009) "Monitoring SAW-actuated microdroplets in view of biological applications," Sensors and Actuators B: Chemical, 138(1), 374-382.
Renaudin et al.(2006) "SAW nanopump for handling droplets in view of biological applications," Sensors and Actuators B, 113: 389-397.
Sankaranarayanan et al., (2008) "Flow induced by acoustic streaming on surface-acoustic-wave devices and its applications in biofouling removal: A computational study and comparisons to experiment," Phys. Rev. E Stat. Phys. Plasmas Fluids Relat. Interdiscip. Topics 77: 066308-19.
Scheerschmidt et al., (2010) "Resonance modes of magnetically generated surface waves in acoustic wave guide systems," Journalism of Magnetism and Magnetic Materials, 322: 1628-1630.
Schneider et al., (2008) "An Acoustically Driven Microliter Flow Chamber on a Chip—FCC) for Cell-Cell and Cell-Surface Interaction Studies," Chem. Phys. Chem., 9: 641-645.
Sethu et al., (2004) "Continuous Flow Microfluidic Device for Rapid Erythrocyte Lysis," Anal. Chem. 76: 6247-6253.
Shi et al.,(2009) "Acoustic tweezers: patterning cells and microparticles using standing surface acoustic waves (SSAW)," Lab Chip, 9: 2890-2895.
Shi et al., (2008) "Focusing microparticles in a microfluidic channel with standing surface acoustic waves (SSAW)," Lab on a Chip, 8: 221-223.
Shilton et al., (2008) "Particle concentration and mixing in microdrops driven by focused surface acoustic waves," J. Appl. Phys., 104: 014910-9.
Shiokawa et al. (1989) "Liquid streaming and droplet formation caused by leaky Rayleigh waves," Proc IEEE Ultrason. Symp., 641: 643-646.
Blamey et al., (2013) "Microscale Capillary Wave Turbulence Excited by High Frequency Vibration," American Chemical Society, 29: 3835-3845.
Boe et al., (2001) "European Respiratory Society Guidelines on the use of nebulizers," ERS Journals, 18:228-242.
Brun et al., (2000) "A review of the Technical Aspects of Drug Nebulization," Pharmacy World & Science, 22(3): 75-81.
Cheng et al., (1998) "Preparation and hybridization analysis of DNA/RNA from E. coli on microfabricated bioelectronic chips," Nature Biotechnology, 16: 541-546.
Dolovich & Dhand (2011) "Aerosol drug delivery: developments in device design and clinical use," 377: 1032-1045.
Eixarch et al., (2010) "Drug Delivery to the Lung: Permeability and Physicochemical Character-istics of Drugs as the Basis for a Pulmonary Biopharmaceutical Classifica-tion System (PBCS)," Journal of Epithelial Biology & Pharmacology 3: 1-14.
Graham-Rowe (2006) "An Ultrasonic Tourniquet to Stop Battlefield Bleeding," Rewriting Life pp. 5.
Ju et al., (2008) "Sensors and Actuators A: Physical," Sensors and Actuators A, 570-575.

(56) References Cited

OTHER PUBLICATIONS

Ju et al., (2010) "A Study on Atomization Characteristics of Surface Acoustic Wave Atomizer using Laser Doppler Anemometry," 309-312.
Kurosawa et al., (1997) "Characteristics of Liquids Atomization Using Surface Acoustic Wave," International Conference, 2: 801-804.
Maehara et al., (1986) "Influence of the vibrating system of a multipinholeplate ultrasonic nebulizer on its performance," Rev. Sci. Instrum. 57(11): 2870-2876.
Qi et al., (2008) "Interfacial destabilization and atomization driven by surface acoustic waves," Physics of Fluids, 20(7): 074103-14.
Rajapaksa et al., (2014) "Effective Pulmonary delivery of an aerosolized plasmid DNA vaccine via surface acoustic wave nebulization," Respiratory Research, 1-12.
Reboud et al., (2012) "Nebulisation on a disposable array structured with phononic lattices," Lab on a Chip, 12: 1268-1273.
Reboud et al., (2012) "Shaping acoustic fields as a toolset for microfluidic manipulations in diagnostic technologies," PNAS, 1-6.
Standard F756-08, (2009) "Standard Practice for Assessment of Hemolytic Properties of Materials," ASTM: 1-5.
Topp (1973) "Ultrasonic Atomization—A Photographic Study of the Mechanism of Disintegration," Aerosol Science 4: 17-25.
International Search Report PCT/EP2015/076359 16 pages.
Wu et al., (2005) "Surface acoustic wave band gaps in micro-machined air/silicon phononic structures—theoretical calculation and experiment," Zeitschrift Fur Kristallographie, 220: 841-847.
Wu et al., (2004) Surface and bulk acoustic waves in two-dimensional phononic crystal consisting of materials with general anisotropy, Physical Review B, 69 094301-10.
Yager et al. (2006) "Microfluidic diagnostic technologies for global public health," Nature, 442:412-418.
Yang et al., (2009) "Solution-processed flexible ZnO transparent thin-film transistors with a polymer gate dielectric fabricated by microwave heating," Nanotechnology, 20(46): 465201 1-5.
Yatsuda and Yamanouchi (2000) "Automatic Computer-Aided Design of SAW Filters Using Slanted Finger Interdigital Transducers," IEEE Trans. Ultrason. Ferroelectr. Freq. Control, 47 (1): 140-147.
Yeo and Friend (2009) "Ultrafast microfluidics using surface acoustic waves," Biomicrofluidics, 3, 012002-012002-23.
Yu and Kim (2004) "Ultrasonic underwater thruster," Micro-Electro Mechanical Systems, 17th IEEE International Conference on, 486-489.
Zhang et al., (2009) "Rapid Concentration of particle and bioparticle suspension based on surface acoustic wave," Appl. Acoust., 70: 1137-1142.
Allison et al., (2008) "Ultrasonic Propulsion," AIAA Journal of Propulsion and Power 24: 547-553.
Alvarez et al., (2007) "Microaerosol and Nanoparticle Synthesis for Drug Delivery via Surface Acoustic Wave Atomization," 16th Australasian Fluid Mechanics Conference (AFCM) 621-624.
Alvarez et al., (2008) "Rapid generation of protein aerosols and nanoparticles via surface acoustic wave atomization," Nanotechnology 19: 455103.
Baek et al., (2010) Wireless induction heating in a microfluidic device for cell lysis, Lab on a Chip (10) 909-917.
Batchelor (1951) Note on a class of solutions of the Navier-Stokes equations representing steady rotationallysymmetric flow Q.J. Mech. Appl. Math. 4 29-41.
Benchabane et al., (2005) "Silicon phononic crystal for surface acoustic waves," Ultrasonics Symposium IEEE 2: 922-925.
Benchabane et al., (2006) "Elastic band gaps for surface modes in an ultrasonic lithium niobate phononic crystal," Photonic Crystal Materials and Devices III 6182-18216.
Bennes et al., (2007) Detection and high-precision positioning of liquid droplets using SAW systems, IEE Transactions on Ultrasonics Ferroelectrics and Frequency Control 54(10): 2146-2151.
Beyssen et al., (2005) "Surface acoustic wave microfluidic device," Ultrasonics Symposium IEEE 2: 1028-1031.
Bloch et al., (1979) "Selective Reflection of Surface Acoustic Waves by Periodic Dot Arays," Ultrasonics Symposium IEEE, 687-690.
Borthwick et al., (2005) "Improvement of Immunodetection of Bacterial Spore Antigen by Ultrasonic Cavitation," Anal. Chem.77: 7242-7245.
Bourquin et al., (2011) "Integrated immunoassay using tuneable surface acoustic waves and lensefree detection," Lab Chip, 11: 2725-2730.
Bourquin et al., (2010) "Tuneable surface acoustic waves for fluid and particle manipulations on disposable chips," Lab on aChip.
Bourquin et al., (2011) "Phononic Crystals for Shaping Fluids," Adv Mater 23: 1458-1462.
Chen et al., (2008) "On-line cell lysis and DNA extraction on a microfluidic biochip fabricated by microelectromechanical system technology," Electrophoresis, 29: 1844-1851.
Di Carlo et al., (2003) "Reagentless mechanical cell lysis by nanoscale barbs in microchannels for sample preparation," Lab on a Chip, 3, 287-291.
Ding et al., (2013) "Surface acoustic wave microfluidics," Lab on a Chip, 13, 3626-3649.
Djafari-Rouhani et al., (2008) "Absolute band gaps and waveguiding in free standing andsupported phononic crystal slabs," Photonics and Nanostructures—Fundamentals and Applications 6:32-37.
Dogheche et al., (2002) "Thick LiNbO3 layers on diamond-coated silicon for surface acoustic wave filters" Applied Physics Letters, 81 (7): 1329-1331.
Du et al., (2007) "ZnO film for application in surface acoustic wave device," Journal of Physics: Conference Series, 76: 012035 1-6.
Du et al., (2009) "Microfluidic pumps employing surface acoustic waves generated in ZnO thin films," Journal of Applied Physics, 105(2), 024508-7.
Eckart et al., (1948) "Vorticies and Streams Caused by Sound Waves", Phys. Rev. 73(1): 68-76.
Ehlers and Koiller (2011) "Could cell membranes produce acoustic streaming? Making the case for Synechococcus self-propulsion," Math Comput Model, 53: 1489-1504.
Siegrist et al., (2010) "Validation of a centrifugal microfluidic sample lysis and homogenization platform for nucleic acid extraction with clinical samples," Lab on a Chip, 10: 363-371.
Sinclair (2000) "A high force low area MEMS thermal actuator," Seventh Intersociety Conf. on Thermal and Thermomechanical Phenomena in Electronic Systems1: 127-132.
Smith et al., (1969) "Analysis of Interdigital Surface Wave Transducers by Use of an Equivalent Circuit Model," IEEE T. Microw. Theory, 17(11): 856-864.
Sritharan et al., (2006) "Acoustic mixing at low Reynold's numbers," Applied Physics Letters, AIP, American Institiute of Physics, 88(5): 54102-054102.
Strobl et al., (2004) "Nano- and Pico-Dispensing of Fluids on Planar Substrates Using SAW," IEEETrans. Ultrason, Ferroelect. Freq. Control, 51(11): 1432-1436.
Su et al., (2002) "A water-powered osmotic microactuator," J Microelectromech Syst., 11(6): 736-742.
Tai and Muller (1989) "IC-processed electrostatic synchronous micromotors," Sens Actuators 20:49-55.
Tan and Hoover (2010) "Thrust and wake characterisation in small, robust ultrasonic thrusters" IEEE Oceans, 1-9.
Tan et al. (2009) "Interfacial Jetting Phenomena Induced by Focused Surface Vibrations," Physical Review Letters, 103(2), 024501-4.
Tan et al., (2007) "Microparticle collection and concentration via a miniature surface acoustic wave device," Lab on a Chip, 7(5): 618-625.
Taylor et al. (2001) "Lysing Bacterial Spores by Sonication through a Flexible Interface in a Microfluidic System," Analytical Chemistry, 73(3), 492-496.
Überall (1973) "Surface Waves in Acoustics," Phys. Acoustics: principles and methods, 10:1-60.
Vasseur et al., (2008) "Absolute forbidden bands and waveguiding in two-dimensional phononic crystal plates," Physical Review B, 77(8), 085415-15.

(56) References Cited

OTHER PUBLICATIONS

Waters et al., (1998) "Microchip Device for Cell Lysis, Multiplex PCR Amplification, and Electrophoretic Sizing," Anal Chem., 70 (1): 158-162.
Watson and Yeo (2009) "Piezoelectric ultrasonic resonant motor with stator diameter less than 250 m: the Proteus motor," J Micromech Microeng 19: 022001 1-5.
Watson et al., (2010) "Modelling and testing of a piezoelectric ultrasonic micro-motor suitable for in vivo microrobotic applications," J. Micromech. Microeng, 20: 115018 1-16.
Wilson et al. (2010) "Signal Enhancement of Surface Enhanced Raman Scattering and Surface Enhanced Resonance Raman Scattering Using in Situ Colloidal Synthesis in Microfluidics," Anal. Chem., 82, 2119-2123.
Wilson et al. (2011) "Phononic crystal structures for acoustically driven microfluidic manipulations," Lab Chip, 11, 323-328.
Wilson (1997) "Inhibition and Facilitation of Nucleic Acid Amplification," Applied and Environmental Microbiology, 63(10): 3741-3751.
Wixforth et al., (2003) "Flat fluidics: a new route toward programmable biochips," Microfluidics, BioMEMS, and Medical Microsystems 4982: 235-242.
Wixforth (2006) "Acoustically Driven Programmable Microfluidics for Biological and Chemical Applications," Journal of the Association for Laboratory Automation, 11:399-405.
Wixforth (2003) "Acoustically-driven planar microfluidics," Superlattices and Microstructures 33, 389-396.
Wu et al., (2009) "Utilization of phononic-crystal reflective gratings in a layered surface acoustic wave device", Applied Physics Letters, AIP, American Institiute of Physics, Melville, NY, US, vol. 94, No. 10: 101913-101913.
Wu et al., (2006) "Design of a highly magnified directional acoustic source based on the resonant cavity of twodimensional phononic crystals," Appl. Phys. Lett. 89:171912-171913.
Wu and Chang (2005) "Actuating and detecting of microdroplet using slanted finger interdigital transducers," Journal of Applied Physics, 98(2): 024903-7.
Wu et al., (2005) "Frequency band-gap measurement of two-dimensional air/silicon phononic crystals using layered slanted finger interdigital transducers," Journal of Applied Physics, 97(9): p. 7.
http://medicalphysicsweb.org/cws/article/research/26443 (2006) "Ultrasound that won't have you in stitches," MedicalPhysicsWeb.pdf.
http://www.arobella.com/products/qoustic-description.htm (2007) "Qoustic Wound Therapy System," Arobella Medical, LLC 3 pages.
http://www.misonix.com/medical/products/sonicone/ "Top-Down Ultrasonic Wound Debridement Means Better Outcomes," SonicOne Family Brochure 6 pages.
UKIPO Search report on GB0914762.0, dated Dec. 15, 2009 6 pages.
International Search Reporton PCT/GB2010/001600, dated Sep. 2, 2011 18 pages.
International Search Report on PCT/GB2012/000192, dated Jun. 1, 2012 9 pages.
International Search Report on PCT/GB2012/051133, dated May 18, 2012 13 pages.
UKIPO Search report on GB1103211.7, dated Jun. 30, 2011 8 pages.
UKIPO Search report on GB1108462.1, dated Sep. 6, 2011 8 pages.
UKIPO Search report on GB1221614.9, dated Mar. 7, 2013 6 pages.
UKIPO Search report on GB1315755.7, dated Feb. 26, 2014 3 pages.
CN 201080048009.X dated Aug. 26, 2013 First Office Action, dated Aug. 26, 2013 9 pages.
http://www.celleration.com/mist-therapy/-Mist Therapy Accelleration. pdf.
Graham-Rowe, Duncan, (2006) "An Ultrasonic Tourniquet to Stop Battlefield Bleeding", MIT Technology Review.
GB Search Report for Application No. GB1420061.2, Search Report dated Apr. 24, 2015, 3 pages.
Ho et al., (2011) "Paper-based microfluidic surface acoustic wave sample delivery and ionization source for rapid and sensitive ambient mass spectrometry" Supplemental Info.: 1-12.
International Search Report (dated 2016) PC/EP2015/076359: 1-16.
AU Exam Report (dated 2019) AU2015345130: 1-3.

* cited by examiner

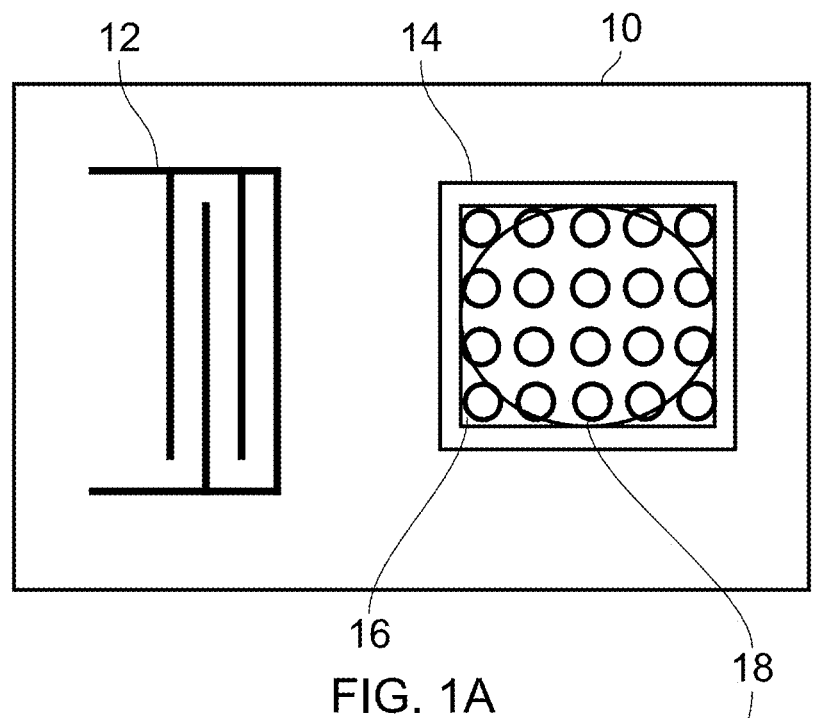
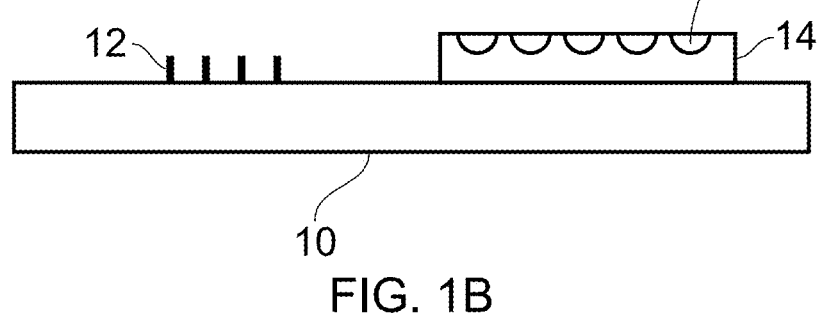
FIG. 1A
FIG. 1B

NEBULISATION OF LIQUIDS

CROSS-REFERENCE TO RELATED APPLICATIONS

This application is a continuation of U.S. application Ser. No. 15/525,509, filed May 9, 2017, which is the U.S. national phase under 35 U.S.C. § 371 of PCT International Application No. PCT/EP2015/076359, which has an international filing date of Nov. 11, 2015 and designated the United States of America, which application claims benefit of priority to GB Application No. 1420061.2, filed Nov. 11, 2014, the disclosures of each of which are incorporated by reference herein.

BACKGROUND TO THE INVENTION

Field of the Invention

The present invention relates to devices and methods for nebulising liquids and liquid suspensions. The invention has particular, but not necessarily exclusive, applicability to the preparation of therapeutic agents suitable for delivery to subjects.

Related Art

According to the World Health Organization (WHO) there are 235 million people suffering from asthma and 64 million people with chronic obstructive pulmonary disease (COPD), leading to 3 million deaths per year worldwide. Many millions also suffer with pulmonary infectious disease, cystic fibrosis, pulmonary hypertension and allergic rhinitis as well as other under-diagnosed chronic respiratory diseases. Estimates of the cost of treating patients with such lung diseases, including those caused by tuberculosis (TB), COPD, cystic fibrosis, pneumonia, asthma and smoking was Euro 380 billion per annum (according to the European Lung White Book of the European Respiratory Society erswhitebook.org/ [accessed 12 Aug. 2014]).

Generally, patients with such respiratory diseases can be treated by the inhalation of aerosols or by alternate non-lung target routes such as oral and intravenous. One of the major advantages of the inhalation pulmonary route is that it can be targeted directly to the lung, and indeed, effective delivery of medication has been shown to be crucially dependent upon the droplet size distribution within the aerosol of medicine [Brun et al 2000]. In general, if the size is too small (<0.5 μm), the droplet will be exhaled, whilst if the size is too large (>5.0 μm), the droplet will be trapped in the upper respiratory tract or throat. The accepted wisdom is that pulmonary drug delivery requires droplet size distribution of the aerosols with diameters between about 1 and 5 μm. Generating droplets of the optimum size allows medicine to reach and stay in the lungs at the correct therapeutic dose.

In addition to drug delivery, there are many other therapeutic strategies that would benefit from localised and effective lung delivery through inhalation of aerosols. For example, both gene- and RNA-focused therapies can be targeted directly into the lung, providing an appealing strategy for therapy. However, the efficiency of the approach, coupled with the breadth/limitation of cell type(s) that are required to be targeted for therapeutic efficacy are important considerations. For example, targeting the lung epithelium in cystic fibrosis patients is extremely difficult due to certain anatomical and pathological challenges and, as a consequence, has limited the clinical data obtained with a range of gene therapy approaches at both the pre-clinical and clinical level. Alternatively, targeting vascular cells is also appealing for treating patients with pulmonary arterial hypertension, although, again, effective delivery to the blood vessels necessitates that the therapeutic system (or droplet) has to transit defined and substantial anatomical barriers.

Thus, in short, there is a significant potential for improving the delivery of drugs and biologics (including genes and RNA) by preparing substantially monodisperse aerosol droplets that are able to enter the appropriate tissue within the lung. Such a technique would enable new therapies, providing access to a substantial market allowing the reduction of healthcare costs and the improvement of clinical outcomes.

SUMMARY OF THE INVENTION

The present invention has been devised in order to address at least one of the above problems. Preferably, the present invention reduces, ameliorates, avoids or overcomes at least one of the above problems.

The present invention is based on the inventors' findings that the controlled actuation of a liquid suspension placed in an array of suitable cavities and excited by surface acoustic waves at suitable frequencies can provide nebulised droplets of the liquid suspension with a tight distribution of droplet size.

The present invention has arisen from the inventors' work on fluid manipulation using surface acoustic waves, disclosed in WO 2011023949, WO 2011060369, WO 2012114076 and WO 2012156755, the entire content of each of which is hereby incorporated by reference.

Nebulisers are used to administer medication or other therapies in the form of a mist inhaled into the lungs. These devices are currently used to deliver various drugs for the treatment of cystic fibrosis, asthma, COPD and other respiratory diseases [Bo et al (2001)]. Nebulizers use oxygen, compressed air or ultrasonic power to break up medical solutions and suspensions into small aerosol droplets that can be directly inhaled from the mouthpiece of the device.

There are considered to be four main nebuliser systems available at the time of writing [Dolovich and Dhand (2011)]—conventional (using compressed air); ultrasonic (using crystals to vibrate the medication to a mist); vibrating mesh technology (using a vibrating metal mesh to create a mist of droplets from medication) and adaptive aerosols (using vibrating technology mesh combined with optimal breathing monitoring).

All four classes of current nebuliser systems have limitations in the amount of drug that they can deliver to the lung, which is typically 70%-80% of the dose. For patients this results in sub-optimal treatment regimes with consequent impact on health and wellbeing. A particular disadvantage of the ultrasonic nebuliser is that it is unable to nebulise suspensions and liquid with high viscosity and surface tension [Reboud, Wilson et al (2012); Reboud, Bourquin et al (2012); Qi et al (2008)]. Additionally, the present inventors consider that the droplet size distribution provided by current nebuliser systems is too broad.

In the preferred embodiments of the present invention, there is provided control over the aerosol droplet size and size distribution. Accordingly, the present invention has the potential to provide patients with better [>95%] delivery of active drug per dose, thereby improving treatment outcomes e.g. infection control in cystic fibrosis or managing asthmatic conditions.

In a first preferred aspect, the present invention provides a device for the preparation of nebulised droplets, the device having:

a surface acoustic wave (SAW) transmission surface;
a SAW transducer adapted to generate and propagate SAWs along the SAW transmission surface; and
an array of cavities opening at the SAW transmission surface for containing a liquid, wherein, in operation, SAWs propagating along the SAW transmission surface interact with the liquid in the cavities to produce nebulised droplets of the liquid.

In a second preferred aspect, the present invention provides a method for the preparation of nebulised droplets, including providing a device having a surface acoustic wave (SAW) transmission surface, a SAW transducer adapted to generate and propagate SAWs along the SAW transmission surface, and an array of cavities opening at the SAW transmission surface, the method including the steps:

containing a liquid in the cavities; and
causing SAWs to propagate along the SAW transmission surface to interact with the liquid in the cavities to produce nebulised droplets of the liquid.

In a third preferred aspect, the present invention provides a method for the preparation of nebulised droplets and their delivery to a subject for therapeutic treatment, including providing a device having a surface acoustic wave (SAW) transmission surface, a SAW transducer adapted to generate and propagate SAWs along the SAW transmission surface, and an array of cavities opening at the SAW transmission surface, the method including the steps:

containing a liquid in the cavities;
causing SAWs to propagate along the SAW transmission surface to interact with the liquid in the cavities to produce nebulised droplets of the liquid; and
delivery of the nebulised droplets to the subject for therapeutic treatment by inhalation.

In a fourth preferred aspect, the present invention provides a medicament in liquid form for use in a method for the preparation of nebulised droplets of the medicament and their delivery to a subject for therapeutic treatment, including providing a device having a surface acoustic wave (SAW) transmission surface, a SAW transducer adapted to generate and propagate SAWs along the SAW transmission surface, and an array of cavities opening at the SAW transmission surface, the method including the steps:

containing the medicament in the cavities;
causing SAWs to propagate along the SAW transmission surface to interact with the medicament in the cavities to produce nebulised droplets of the liquid; and
delivery of the nebulised droplets to the subject for therapeutic treatment by inhalation.

Preferably, the medicament is for treatment of one or more conditions selected from the group consisting of: asthma; chronic obstructive pulmonary disease (COPD); pulmonary infectious disease; cystic fibrosis; pulmonary hypertension; allergic rhinitis; other chronic respiratory diseases; pneumonia; tuberculosis (TB); lung disease such as lung disease caused by smoking; diabetes; acute or chronic pain; multiple sclerosis; osteoporosis; infectious disease.

Preferably, the medicament comprises one or more compounds selected from the group consisting of:

Hydrocortisone ($C_{21}H_{30}O_5$);
Testosterone ($C_{19}H_{28}O_2$);
Dexamethasone ($C_{22}H_{29}FO_5$);
Budesonide ($C_{25}H_{34}O_6$);
Betamethasone ($C_{22}H_{29}FO_5$);
Cromolyn ($C_{23}H_{16}O_{11}$);
Formoterol ($C_{19}H_{24}N_2O_4$);
Imipramine ($C_{19}H_{24}N_5$);
Losartan ($C_{22}H_{23}ClN_6O$);
Terbutaline ($C_{12}H_{19}NO_3$);
Salbutamol ($C_{13}H_{21}NO_3$);
Zopiclone ($C_{17}H_{17}ClN_6O_3$);
Zaleplon ($C_{17}H_{15}N_5O$);
Zolpidem ($C_{19}H_{21}N_3O$);
Leflunomide ($C_{12}H_9F_3N_2O_2$);
Oxymetazoline ($C_{16}H_{24}N_2O$);
Insulin;
Morphine;
Interferon Beta 1a;
Parathyroid hormone;
Nicotine;
One or more antibiotics;

and pharmaceutically acceptable derivatives and salts thereof, optionally including excipients and carriers such as nanoparticles.

A review of candidate pharmaceutical compositions for pulmonary delivery is set out in Eixarch et al (2010), the entire content of which is hereby incorporated by reference.

The first, second, third and/or fourth aspect of the invention may be combined with each other in any combination. Furthermore the first, second, third and/or fourth aspect of the invention may have any one or, to the extent that they are compatible, any combination of the following optional features.

The liquid may be one or more of: a pure compound; a mixture of liquids; a solution of one or more solutes in a liquid solvent; a suspension of particles (solid, substantially solid or liquid) in a carrier liquid; a colloid; an emulsion; nanoparticles or a suspension of nanoparticles.

The SAW transmission surface may be a surface of the SAW transducer. However, more preferably, the SAW transmission surface is a surface of a superstrate coupled to the SAW transducer.

The present invention is not necessarily limited to any particular orientation. The term "superstrate" is used because in typical implementations of embodiments of the invention, this item is placed on top of the SAW transducer. However, other orientations are contemplated, e.g. in which a corresponding substrate is placed under the transducer, yet the same effect of the invention can seen, in which the sample is nebulized from cavities in the surface of the substrate. Furthermore, the present invention is not necessarily limited to a planar configuration. For example, the transducer may be formed inside the superstrate, e.g. in a tubular configuration. Alternatively, the transducer may be formed around the superstrate, with the superstrate in the form of a tube (or hollow needle) held inside a transducer tube. This may be preferred, in order that a continuous (or quasi continuous) supply of sample fluid may be provided to the superstrate tube, with the nebulized plume provided at a free end of the superstrate tube.

Preferably, the superstrate is formed of a material which is impervious to the liquid. This helps to avoid any (potentially contaminating) contact between the transducer and the liquid.

Preferably, the transducer comprises a layer of piezoelectric material. For example, the layer of piezoelectric material may be a sheet (e.g. a self-supporting sheet) of piezoelectric material. The layer of piezoelectric material may be a single crystal, such as a single crystal wafer. A suitable material is $LiNbO_3$. A preferred orientation for the cut for this material is Y-cut rot. 128°. This has a higher electromechanical coupling coefficient than other orientations. Other ferroelectric materials may be used, e.g. PZT, BaTiO$_3$, SbTiO$_3$ or ZnO. Still further, materials such as SiO$_2$ (quartz), AlN, LiTaO$_3$, Al$_2$O$_3$ GaAs, SiC or polyvinylidene fluoride (PVDF) may be used. As an alternative to a single crystal, the material can be provided in polycrystalline or even amorphous form, e.g. in the form of a layer, plate or film.

The transducer preferably further comprises at least one arrangement of electrodes. For example, the electrodes may be interdigitated. More preferably, the transducer comprises two or more arrangements of electrodes. In some embodiments, it is preferred that the transducer is tunable, such that the lateral position of the SAWs emission train is movable. For example, the slanted interdigitated arrangement of electrodes suggested by Wu and Chang (2005) can be used for the transducer.

The superstrate may be permanently coupled to the piezoelectric layer, in the sense that it is not removable from the piezoelectric layer without damage to the device.

Alternatively, coupling between the transducer and the superstrate may be achieved using a coupling medium, preferably a fluid or gel coupling medium. The coupling medium may be an aqueous coupling medium, e.g. water. Alternatively, the coupling medium may be an organic coupling medium, such as an oil-based coupling medium or glycerol. The coupling medium provides intimate contact between the superstrate and the transducer and allows the efficient transfer of acoustic energy to the superstrate from the transducer.

The advantage of providing the superstrate as a separate entity from the transducer is very significant. Typical SAW transducers are complex to manufacture. For this reason, they are typically expensive. Contamination of the transducer may be difficult or impossible to remove, if the liquid is allowed to come into contact with the transducer. Alternatively, removal may not be cost-effective, or may damage the transducer. However, it is strongly preferred that the transducer can be re-used. Accordingly, it is preferred that the liquid does not contact the transducer but instead contacts the superstrate coupled to the transducer. The superstrate itself may be disposable (e.g. disposed of after a single use). The superstrate may be formed by various methods, such as microfabrication, embossing, moulding, spraying, lithographic techniques (e.g. photolithography), etc.

The cavities preferably have substantially the same shape. The SAW transmission surface, in use, preferably is held substantially horizontal. In this way, the cavities preferably open in the upward direction. The cavities may be closed at an end distal from the SAW transmission surface. Alternatively, the cavities may be open at an end distal from the SAW transmission surface.

The cavities may be substantially columnar in shape. In this way, the cross sectional shape of the cavities may be substantially uniform with depth (a direction perpendicular to the SAW transmission surface). For example, the cross sectional shape of the cavities in the depth direction may be rectangular, square, rounded, oval, elliptical, circular, triangular. Most preferably the cross sectional shape of the cavities in the depth direction is circular. The cross sectional area of the cavities may be uniform with depth. However, in some embodiments this may not be the case, allowing the cavities to have a cross sectional area which narrows, expands or undulates with depth. For example, funnel-shaped cavities may be provided (such cavities being capable of being formed using a KOH etch for example), to provide suitable volume in the cavity to retain the liquid.

The cavities may have an internal structure. For example, there may be provided one or more pillars upstanding in the cavities, walls projecting into the cavities or other projections into the cavities. The internal walls of the cavities may have one or more array of such projections. The array of projections may be considered to be a phononic structure, in the sense that it is based on a periodic arrangement (in the manner disclosed in WO 2011023949, WO 2011060369, WO 2012114076 and WO 2012156755) for affecting the distribution and/or transmission of SAWs in the cavities. In the case of one or more pillars, there may be provided one or more support struts extending to the pillar to hold it in position. This is particularly the case if the cavity has two open ends (i.e. extends through the superstrate) since in this case there is no base of the cavity for the pillar to be supported on.

Such internal structure interact with the liquid and with the SAWs in a manner which can further improve the performance of the cavities in restricting the droplet size distribution.

The cavities preferably have substantially the same dimensions.

Preferably the depth of the cavities is at least 1 µm. Preferably the depth of the cavities is at most 1 mm, more preferably at most 500 µm. In some embodiments, the cavities can be blind cavities. However, in other embodiments the cavities can open at a surface opposite to the SAW transmission surface. This is preferred, for example, where the liquid to be nebulised is fed to the cavity from one or more reservoirs.

Preferably the maximum dimension of the cavities in a direction perpendicular to the depth of the cavities is at least 1 µm. This lower limit is set in view of the preferred lower limit for droplet size. The lower limit may be at least 2 µm, at least 5 µm, at least 10 µm, at least 20 µm, at least 30 µm, at least 40 µm or at least 50 µm. Preferably, this maximum dimension is at most 500 µm, more preferably at most 400 µm, at most 300 µm or at most 200 µm. Where the cavities have a circular cross section shape, this dimension is referred to as the diameter of the cavities. Where the cavities have a non-circular cross sectional shape, this maximum dimension is also referred to as the diameter.

The present inventors have considered the effect of this dimension on the efficacy of the invention. Capillary waves, in the context of the present invention, can be considered to be waves which are capable of travelling along the free surface of the liquid, whose dynamics are dominated by surface tension effects. In common terminology, they can be considered to be "ripples" in the manner of ripples on the surface of a body of water. Capillary waves in a body of liquid constrained in a cavity can be produced at a fundamental vibrational mode, and/or at harmonic vibrational modes. Without wishing to be bound by theory, it is considered to be of importance to restrict the ability of the volume of liquid contained in the cavity to support capillary waves at the fundamental mode and preferably also at harmonic modes (particularly lower harmonic modes). This is because it is considered that such capillary waves would otherwise be responsible for the formation of relatively large droplets.

Therefore it is preferred that the diameter of the cavities is suitable to reduce or prevent the formation of such capillary waves in the liquid contained in the cavities. Put simply, at least for relatively low operational frequencies (in the kHz range, for example, i.e. less than 1 MHz), the diameter D of the cavities is preferably less than the wavelength of capillary waves which could otherwise be formed in the liquid at the driving frequency f.

The driving frequency f can be considered to be responsible for the generation of capillary waves at a fundamental mode of vibration and/or at one or more harmonic modes of vibration. The order of the mode of capillary vibration can be denoted m. The frequency of a particular mode of capillary vibration can be denoted $f_m$.

The driving frequency f may be identical to $f_m$, but in many cases f is only loosely correlated with $f_m$. Therefore $f_m$ can vary with respect to f, typically within a range such as:

$$(f_m)^l \leq f \leq (f_m)^h$$

l is the exponent for the lower limit, and l is 0.5, more preferably 0.6, 0.7, 0.8, 0.9 or 1.0. h is the exponent for the upper limit, and h is 1.5, more preferably 1.4, 1.3, 1.2, 1.1 or 1.0.

Preferably, at least the fundamental capillary vibration mode is suppressed. Therefore preferably m=0 at least. However, additionally or alternatively low order harmonic capillary vibration modes may be suppressed. Therefore in some embodiments, one or more of m=1, m=2, m=3, m=4, m=5, m=6, m=7, m=8, m=9, m=10 and optionally higher, applies.

The progression of resonant responses from the fundamental mode upward are provided by the Lamb model, as set out in Blamey et al (2013), which applies in particular to the elastic resonance of a spherical capillary surface but applies within a reasonable approximation in preferred embodiments of the present invention in which the liquid is held in cavities:

$$f_m = \sqrt{\frac{(m+1)(m+2)(m+4)\gamma}{3\pi\rho L^3}}$$

where L, $f_m$ and m are as defined above, $\gamma$ is the surface tension of the liquid in the cavity and $\rho$ is the density of the liquid.

Blarney et al (2013) provides a list of modes, with specific frequencies ($f_m$) and lengths ($L_m$). These are eigenvalues and $L_m$ represent the size of the deformation at the interface. The cavities (diameter D) should preferably be smaller than $L_m$.

The present inventors consider that the effect of locating the liquid in the cavities is that, under a particular SAW excitation frequency f, the liquid is pinned by the cavities, suppressing or forbidding capillary waves which would otherwise form under those conditions, thereby suppressing the generation of large droplets by such capillary waves.

It is considered to be important that liquid emanating from a cavity does not come into contact with neighbouring cavities or liquid from neighbouring cavities. This is because such contact would increase the free surface area of the liquid and as such increase the degrees of freedom and enable larger wavelength capillary waves to form. As such, depth of the cavity or its shape or the surface chemistry close to the nebulising surface can be important to ensure efficient pinning of the contact line. Suitable depth of the cavities can be between 500 and 50 µm. The deeper the cavity (for a particular cross section shape and diameter) the more liquid that can be nebulised in one 'charge'. Through hole-type cavities have been used having a depth of 380 µm, but such a depth is determined by the thickness of the substrate (or superstrate) in which the cavity is formed, rather than a functional limitation.

As mentioned above, preferably the cavities have substantially the same dimensions. However, it is allowable for the cavities to have a distribution of dimensions. In terms of the diameter of the cavities, preferably the standard deviation of the diameter is 40% or less, more preferably 30% or less, more preferably 20% or less.

The cavities can be in the form of cylindrical holes. As indicated above, in some embodiments the holes can be blind holes. In other embodiments, the holes can be holes which open also at an opposing surface to the SAW transmission surface, in order that additional liquid can be fed into the cavities by capillarity. A suitable volume for the cavities in either can be at least 0.5 nl, more preferably at least 1 nl. This volume is preferably at most 50 nl, more preferably at most 20 nl, more preferably at most 10 nl, more preferably at most 5 nl. As an example, a cylindrical hole of diameter 100 µm and depth 300 µm has a volume of about 2 nl.

The array of cavities may not have long range order. In this case, the arrangement of the cavities may be substantially random, in the sense of not being based on a periodic arrangement.

It is preferred that the cavities have an average cavity-to-cavity nearest neighbour spacing (measured from the central axis of each cavity) of at least 10 µm. This is suitable for SAWs in the MHz region (e.g. of frequency of around 100 MHz). More preferably, this spacing is at least 20 µm, at least 40 µm, at least 60 µm, at least 80 µm, or at least 100 µm. This spacing may be at most 5 mm (corresponding to relatively low frequency SAWs), more preferably at most 4 mm, more preferably at most 3 mm, more preferably at most 2 mm, more preferably at most 1 mm, more preferably at most 0.9 mm, at most 0.8 mm, at most 0.7 mm, or at most 0.6 mm. For example, a cavity-to-cavity nearest neighbour spacing in the range 200-500 µm has been shown to be suitable. For higher frequencies, e.g. in the GHz range, smaller spacings are contemplated, e.g. in the range down to at least 1 µm. Spacing between the cavities is considered to be important in order to prevent liquid merging as it escapes from adjacent cavities.

The frequency of the surface acoustic wave may be in the range of about 10 kHz to about 1 GHz, preferably about 1 MHz to about 100 MHz, more preferably about 5 MHz to about 50 MHz, more preferably about 5 MHz to about 20 MHz, more preferably about 15 MHz to about 5 MHz, more preferably between about 13 MHz and about 8 MHz. The frequency of the surface acoustic wave may be about 12 MHz, about 11 MHz, about 10 MHz, about 9 MHz or about 8 MHz.

The SAW transducer may be formed from any suitable material for generating surface acoustic waves. SAWs may be generated, for example, by a piezoelectric process, by a magnetostrictive process, by an electrostrictive process, by a ferroelectric process, by a pyroelectric process, by a heating process (e.g. using pulsed laser heating) or by an electromagnetic process. It is most preferred that the SAW generation material layer is formed from a piezoelectric layer. In the disclosure set out below, the term "piezoelectric layer" is used but is it understood here that similar considerations would apply to SAW generation material layers formed, for example, of magnetostrictive materials. Therefore, unless the context demands otherwise, the optional features set out in relation to the "piezoelectric layer" are to be understood as applying more generally to the SAW generation material layer, when formed of any suitable material.

The present inventors further consider that the present invention is not necessarily limited to the use of SAWs. It is considered that nebulisation using other acoustic waves, such as bulk acoustic waves, is possible using the principles of the present invention. Such acoustic waves are susceptible of manipulation in a similar manner to SAWs. Bulk acoustic waves, for example, give rise to corresponding acoustic waves or displacements at a free surface. Therefore, in the present disclosure, it is to be understood that SAWs are only one example of a suitable acoustic wave which can be used to provide suitable manipulation of a sample. Thus, although in this disclosure the terms "SAW", "surface acoustic wave", "SAWs" and "surface acoustic waves" are used, it is to be understood that these may be substituted or supplemented by the terms "bulk acoustic wave" and "bulk acoustic waves" or the terms "acoustic wave" and "acoustic waves", unless the context demands otherwise.

Preferably, in use, when the SAW transmission surface is facing upwards, the liquid is contained in the cavities such that the free surface of the liquid is below the level of the SAW transmission surface. Thus, it is preferred that the free surface of the liquid is not located at or above the level of the SAW transmission surface. This allows the liquid contained in the cavities to be isolated from each other, forbidding the formation of capillary waves at the liquid contained in the cavities.

The interior surface of the cavities may be treated in order to promote the containment of the liquid in the cavities. For aqueous liquids, preferably the interior surface of the cavities is formed to be hydrophilic. For non-aqueous liquids, preferably the interior surface of the cavities is formed to be hydrophobic.

Additionally or alternatively, the SAW transmission surface may be treated in order to promote the containment of the liquid in the cavities. For example, this treatment may be selectively carried out at the array of cavities intended to contain the liquid. For aqueous liquids, preferably the SAW transmission surface is formed to be hydrophilic. For non-aqueous liquids, preferably the SAW transmission surface is formed to be hydrophobic. Preferably, an area of the SAW transmission surface at which it is not intended for the liquid to be located is formed to be hydrophobic or hydrophilic, respectively, to promote the location of the liquid at the array of cavities intended to contain the liquid.

Preferably, operation of the device results in a nebulised plume of droplets of average diameter in the range 1-5 µm. Preferably, the droplet diameter is measured by laser diffraction. Such measurements provide a droplet size distribution curve in the form of a number-based distribution (i.e. number of droplets is shown on the ordinate and diameter of droplets is shown on the abscissa).

The respirable fraction of the droplets can be defined as the integral of the droplet size distribution in the diameter range 1-5 µm ($N_{1-5}$) divided by the integral of the droplet size distribution over the total diameter range measured ($N_{total}$). Thus, respirable fraction can be defined as ($N_{1-5}$)/($N_{total}$).

Preferably, operation of the device results in a nebulised plume of droplets with a respirable fraction of at least 80%, preferably at least 85%, more preferably at least 90%, more preferably about 95% or higher.

In the prior art, it is known to filter out larger droplets from a nebulised plume in order to restrict the droplet size distribution which reaches the subject. However, this reduces the efficiency of the device, by reducing the proportion of the dose which reaches the subject, and clogging is also a problem, wherein captured large droplets prevent subsequent smaller droplets from being passed through. In the present invention, it is preferred that the respirable fraction is determined on the basis of the nebulised plume formed from the cavities, and not subjected to filtration prior to determination of the droplet size distribution.

In preferred embodiments, the present invention may provide supply of liquid for nebulisation. Since the cavities are relatively small, it may be preferred to ensure a supply of additional liquid for nebulisation. This supply may be continuous, in the sense that liquid is supplied to the cavities for nebulisation while nebulisation is being carried out. Alternatively, this supply may be intermittent, in the sense that liquid is supplied to the cavities after some liquid has been nebulised from the cavities and before nebulisation of the additional liquid is begun. This alternative approach can be considered to be a repeating nebulisation approach.

Preferably, the device is capable of nebulising the liquid at a rate of at least 5 ml/min.

The liquid may have relatively high viscosity, because the mechanism of the nebulisation provided in the present invention can tolerate relatively high viscosity. The viscosity of the liquid (measured at room temperature) may be at least 0.5 mPa·s, but in some embodiments may be at least 1 mPa·s, at least 5 mPa·s, or at least 10 mPa·s. For reference, at room temperature ethanol has viscosity of 1.07 mPa·s, bovine serum albumin 5% in phosphate buffer has viscosity of 1.5 mPa·s, glycerol has viscosity of 1200 mPa·s and water has viscosity of 0.894 mPa·s.

The surface tension of the liquid (measured at room temperature) may be at least 10 mN/m. In some embodiments, the surface tension may be at least 50 mN/m. For reference, at room temperature ethanol has a surface tension of 22.1 mN/m, bovine serum albumin 5% in phosphate buffer has a surface tension of 55.0 mN/m, glycerol has a surface tension of 63.0 mN/m and water has a surface tension of 71.9 mN/m.

The supply of liquid may be provided, for example, by a syringe pump. Other metered liquid supply systems may be used.

In order to supply additional liquid to the cavities, it is possible for the cavities to be open at their end distal from the SAW transmission surface. In that case, the distal ends of the cavities may be in fluid communication with a reservoir of the liquid, to be drawn up by capillarity into the cavities to replace liquid lost by nebulisation. In this case, it is possible for the liquid to be used as the coupling agent for the superstrate.

In order to provide adequate rate of nebulisation, the device may include a plurality of arrays of cavities, in order that there is a suitable number of cavities operating to contribute to the rate of nebulisation (in terms of the volume of liquid nebulised in total by the device per unit time). These may each be associated with a corresponding respective SAW transducer. However, it is possible for the plurality of arrays of cavities to be operated using a single SAW transducer. In order to provide a suitable distribution of SAWs to the respective arrays of cavities, the device may include phononic arrays, as set out in WO 2011023949, WO 2011060369, WO 2012114076 and/or WO 2012156755, in order to concentrate the SAW distribution as required at the respective arrays of cavities.

Further optional features of the invention are set out below.

BRIEF DESCRIPTION OF THE DRAWINGS

Embodiments of the invention will now be described by way of example with reference to the accompanying drawings in which:

FIG. 1A shows a schematic plan view of a device according to an embodiment of the invention, in the form of an etched array of cavities in a superstrate on an interdigitated electrode transducer (IDT) surface.

FIG. 1B shows a cross sectional view of the device of FIG. 1A.

Figure 2:
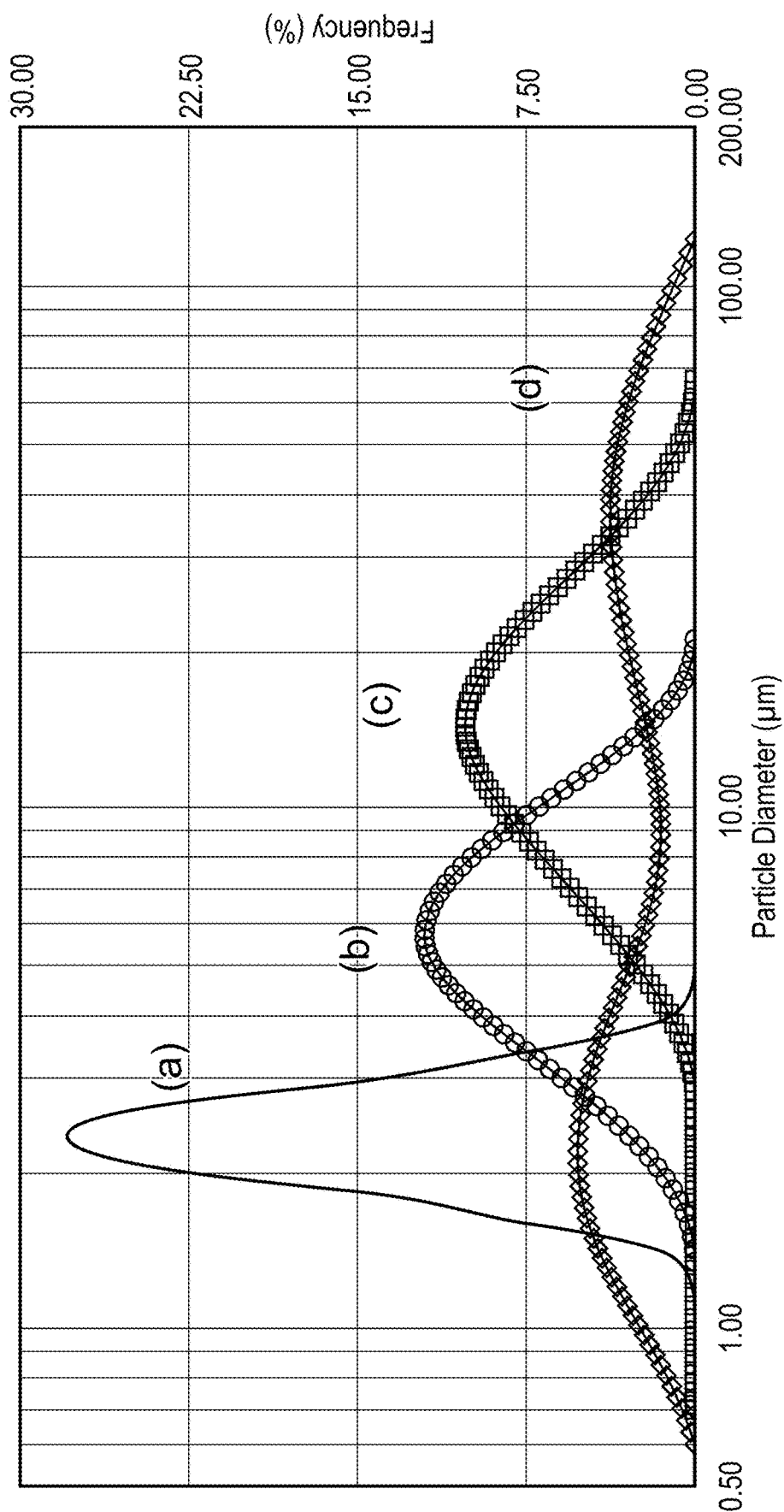
FIG. 2 shows the results of droplet size distribution (number-based) analysis of droplets generated from nebulisation (a) an embodiment of the present invention, with the liquid contained in cavities in a silicon superstrate coupled on a SAW device with excitation frequency of 8.6 MHz and input power of 1.5 W (b) Medix nebuliser (c) Medisana nebuliser and (d) directly on the SAW device of (a) with excitation frequency of 8.6 MHz and input power of 1.5 W.

DETAILED DESCRIPTION OF THE PREFERRED EMBODIMENTS, AND FURTHER OPTIONAL FEATURES OF THE INVENTION

Before discussing the features of the preferred embodiments of the present invention in detail, it is useful to consider the features and performance of known ultrasonic nebulisers.

Ultrasonic nebulisers use the basic principle of applying a high frequency mechanical vibration to a surface. This leads to the excitation of deformations on the free liquid surface that result in microjets [Topp (1973)]. These nebulisers enable the atomisation of a wider range of liquids than other types of nebulisers (such as jet or compressed air). However the aerosol produced suffers from wide range of droplet size. Recently this principle has been extended to the use of SAWs [Reboud, Wilson et al (2012); Qi et al (2009)], which offer the advantages of lower powers and more versatility in integration of preparation functions. However these suffer from similar limitations in the control of the drop size, which generally leads to large mean diameters (above 10 μm) and multiple modes.

To provide a tight droplet size distribution, meshes have been introduced as passive filters (MICROAIR® filter (Omron Healthcare, Inc., Kyoto, Japan), and MICROFLOW filter (Pfeiffer Vacuum GmbH, Annecy, France)) situated after the nebulization process, to select the drops of the correct size. These systems require careful maintenance (to prevent clogging) and show limited efficiency.

Vibrating meshes combine both approaches at the site of nebulisation [Maehara et al (1986)]. A mesh of apertures is vibrated at ultrasonic frequencies to generate the aerosol from a pinching off of the drops through the aperture, in a similar mechanism as the microjets mentioned previously for SAW nebulisation. A similar system is commercialised for droplet dispensing (Scienion AG).

In the preferred embodiments of the present invention, the array of cavities is used to prevent the pinching off enabled by the vibrating meshes and thus provide the opportunity of a reduced size without requiring fine apertures (on the order of the size of the drop dispensed). This provides a cheaper manufacturing strategy. It is also not reliant on the surface properties of the mesh and thus can tolerate conditions that would lead to significant clogging, enabling the dispensing on difficult suspensions, such as those with high viscosity.

Qi et al [2009] have shown nebulisation off a paper superstrate, using SAW. Although the paper superstrate could be viewed as a mesh, their work clearly show no capillary wave limiting effect on the selection of droplet sizes (see FIG. 6 of Qi et al [2009], clearly showing large (i.e. greater than 10 μm) droplets). This is due to the wide distribution of pore sizes compared to the embodiments presented here. Indeed, in their work, the paper superstrate is used as a matrix to feed the liquid, while the nebulisation happens in a bulk mode (as a drop—see FIG. 2c of Qi et al [2009]).

A preferred embodiment of the present invention is illustrated schematically in FIGS. 1A and 1B. This is based on the inventors' previous SAW-based systems [see WO 2011023949, WO 2011060369, WO 2012114076, WO 2012156755, Reboud, Wilson et al (2012) and Reboud, Bourquin et al (2012)].

The device includes a LiNbO$_3$ actuator 10 (single crystal, self-supporting) with an interdigitated electrode 12 and a Si superstrate 14, with etched blind holes 16. The holes (i.e. cavities) are arranged in a square periodic lattice array. A liquid (the sample) 18 is positioned inside the cavities. Thus, the height of the liquid in the cavities is less than the depth of the cavities. This is ensured using highly hydrophilic wetting and a small sample volume.

Upon actuation, the SAW propagates on the SAW transmission surface (the upper surface of the actuator 10) and is coupled onto the superstrate 14, via a coupling medium (not shown) such as gel or water or glue or a more permanent fixture (the array of cavities can be deposited on or etched into the piezoelectric layer). The material of the superstrate 14 is preferably acoustically non-dampening (e.g. Si or glass).

The superstrate 14 holding the array of cavities can be fully in contact with the piezoelectric actuator 10 (as shown in FIGS. 1A and 1B) or coupled only using a small overlap.

The SAW then interacts with the liquid contained in the cavities 16. This interaction creates a nebulised plume. Here the cavities are used to prevent the creation of microjets of sizes greater than about 10 μm that result in multimodal droplet distribution. The specific mechanism for this is still under investigation by the inventors. Without wishing to be limited by theory, the present inventors believe that the mechanism is linked to the damping, suppression or forbidding of capillary waves propagating at the free surface of the liquid in the cavities. This capillary mechanism has been reported as the primary mechanism for nebulisation using SAW [Qi et al (2008)], and leads to sizes outside the range of interest for drug delivery.

In more detail, the SAW actuator 10 and the superstrate 14 are manufactured as follows. Positive photoresist, S1818 (Shipley) was used to lithographically define the electrode pattern on the 127.8° Y-cut LiNbO$_3$ substrate. After the resist exposure and development, 10 nm of titanium and 100 nm of gold were deposited and lift-off was performed in acetone.

The superstrate was fabricated using <100> silicon wafer and standard optical photolithography. The array of cavities was constructed using dry etch (STS ICP), down to half the wafer thickness (about 250 μm). Control experiments were carried out on unpatterned superstrates as well as on the LiNbO$_3$ actuator.

In order to control the volumes and shape of drops deposited on the surface as well as to create controlled spatial areas for nebulisation, the superstrate was patterned with a hydrophobic silane using standard optical lithography. The process involved developing the exposed S1818 photoresist (Shipley) and surface treatment in O$_2$ plasma before silanisation in a solution of trichloro (1H, 1H, 2H, 2H perfluorooctyl) silane (Aldrich) in heptane (Aldrich). The superstrate was then rinsed in acetone to create hydrophilic (untreated) spots of varying sizes in the range of 1-15 mm on a hydrophobic surface.

The frequency response of the SAW actuator was observed using a network analyser (E5071C ENA Series, Agilent Technologies). To perform nebulisation of the liquids on the substrate, a high frequency electrical signal was supplied to the electrodes using a MXG Analog Signal Generator (N5181A, Agilent Technologies) and amplifier (ZHL-5W-1, MiniCircuits).

The silicon superstrate and the piezoelectric substrate were assembled with KY-jelly (Johnson & Johnson) between them to provide efficient coupling.

Measurements of droplet size were performed at 8.64 MHz at the input power of 1.5 W. A sessile drop of 3 μL of deionised (DI) water was used for each nebulisation using the embodiment device of the invention. As comparisons, the nebulised droplet size by two commercialised nebulisers, Medix and Medisana were also measured. The Microneb Medix uses a titanium vibrator which oscillates at approximately 180 kHz with input power of 1.5 W to generate the droplet which is then passing through metal alloy mesh. The Medisana is an ultrasonic nebuliser that operates at 100 kHz with input power of 3 W.

The distributions of nebulised droplet with different sizes were measured using a laser diffraction technique (SPRAYTEC laser diffraction system, Malvern Instruments Ltd, Malvern, UK) and represented in the form of a frequency distribution curve.

The diameters of the nebulised droplet has been reported by Kurosawa et al (1995) by using a number distribution. They obtained the linear mean diameter, $D_{10}$ and surface mean diameter, $D_{32}$ of 19.2 μm and 34.3 μm, respectively for tap water nebulised directly on a SAW device with excitation frequency of 9.5 MHz and input power of 2.5 W for 0.1 ml/min nebulisation rate. The droplet size distribution had two modes with peaks at 10 μm and 40 μm which were reported to be due to the capillary wavelength and the intermittent burst drive, respectively. Smaller droplets ($D_{10}$=6.8 μm and $D_{32}$=15.0 μm) were obtained using SAW device with higher excitation frequency of 48 MHz and lower input power of 2.3 W for 170 μl/min nebulisation rate [Kurosawa et al (1997)]. Alvarez et al (2007) successfully nebulised insulin with mean diameter of 4.5 μm using 19.3 MHz SAW device at 0.3 W input power. By using the same image processing technique as previous authors, Ju et al (2008) estimated the mean diameters of nebulised bovine serum albumin (BSA) to be 5.7, 4.4 and 2.7 μm using SAW devices with excitation frequencies of 50, 75 and 95 MHz, respectively. Smaller droplets with mean diameters of 0.36, 0.38 and 0.4 μm were obtained using 10 MHz SAW device with input power of 0.97, 1.00 and 1.03 W, respectively [Ju et al (2010)].

FIG. 2 shows the distribution obtained for the different surfaces used. They are presented as frequency distributions. The results show that both commercial nebulisers, utilising an ultrasonic technology, provide drop sizes above the optimum size for lung penetration (modes above 5 μm). These distribution are also broad, leading to significant wastage of the targeted therapy.

As shown in FIG. 2, SAW nebulisation from a plain surface is able to provide a smaller droplet size than the commercial nebulisers, which would fit the therapeutically-relevant range (between 1 and 5 μm). However this actuation leads to secondary peaks (large sizes above 10 μm), and a broad distribution. These features lead to inefficient nebulisation and wastage of the liquid.

Figure 3:
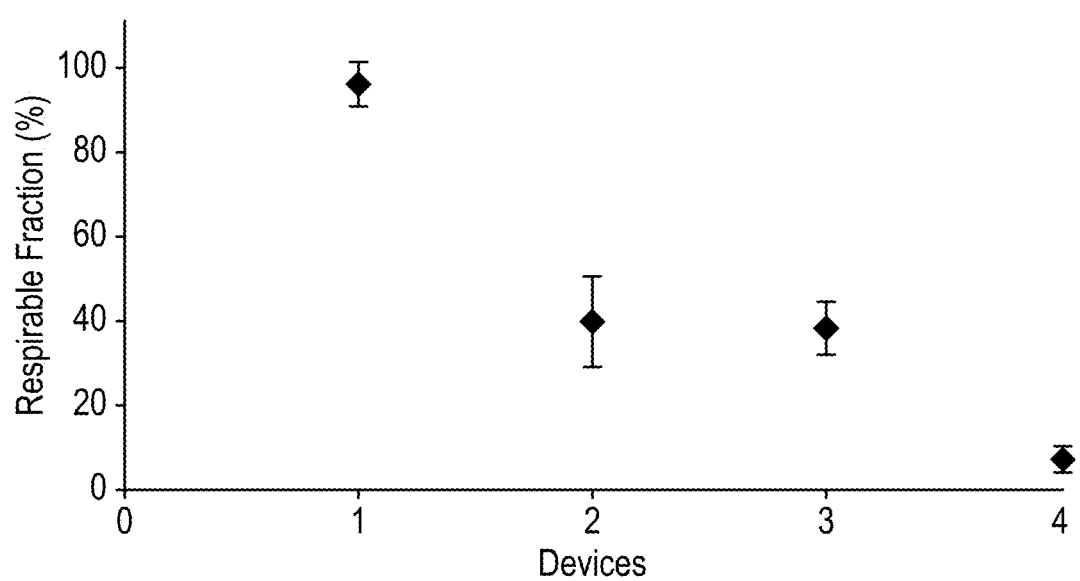
FIG. 3 shows the respirable fraction of nebulised droplet generated from the commercialised nebulisers (Medix (3) and Medisana (4)), directly on SAW devices (2) on silicon superstrate coupled on the SAW device (1) with excitation frequency of 8.6 MHz and input power of 1.5 W
Figure 4A:
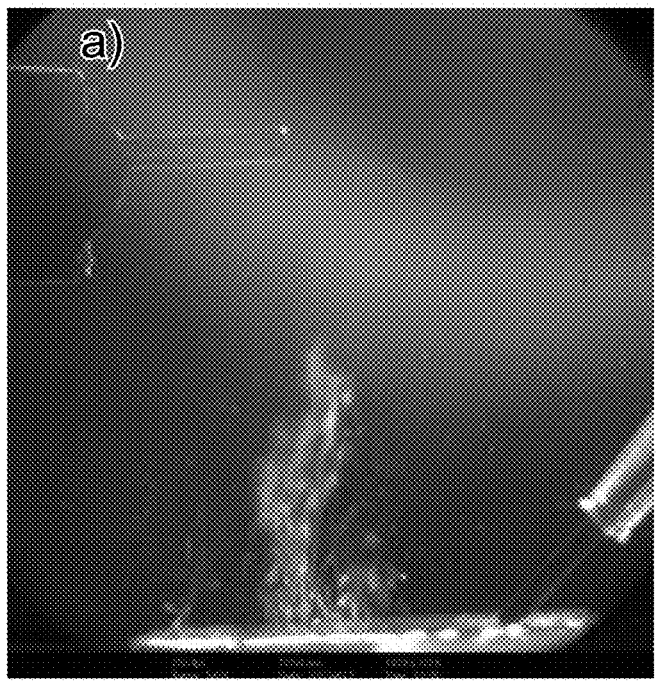
FIG. 4A shows a micrographic image captured from a video of nebulisation at 11.762 MHz and −4 dBm of DI water at 2 μl/min on a plain surface. Large individual drops are seen due to free capillary microjets at the surface of the drop.
Figure 4B:
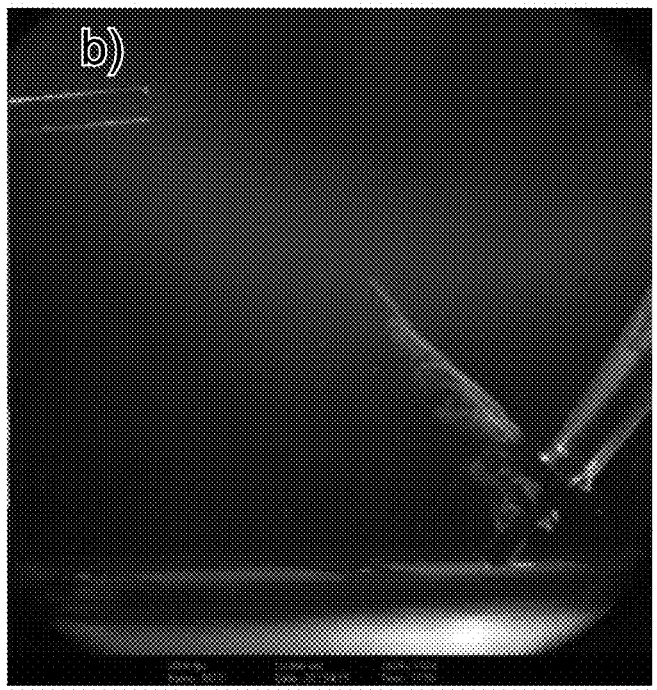
FIG. 4B shows a micrographic image captured from a video of nebulisation at 11.762 MHz and −4 dBm of DI water at 2 μl/min located in cavities arranged as a phononic lattice (900 μm diameter). No large individual drops are seen. As a guide to the scale of the images of FIGS. 4A and 4B, the syringe shown in the image is a 1 ml syringe, with a syringe body diameter of 5 mm.

Using the array of cavities to contain the liquid for nebulisation enables the prevention of large secondary peaks, and sharpens the distribution of the peak (1-5 μm) of interest. The results can be presented using the concept of respirable fraction, which reports the proportion of the total size distribution that is enabled by the different systems (the ratio of integral below the curves between 1 and 5 um, over the total integral), as shown in FIG. 3, while the data analysed is presented in Table 1.

TABLE 1

Derived parameters of the nebulised droplets generated by the surface acoustic waves devices and commercialised nebulisers measured using the SPRAYTEC laser diffraction system (Malvern Instruments Ltd, Malvern, UK).

|  | SAW + Si superstrate with cavities | SAW (transducer only) | MEDIX MICRONEB nebuliser | MEDISANA ® nebuliser |
|---|---|---|---|---|
| Linear mean diameter, $D_v10$ (μm) | 1.81 ± 0.13 | 1.32 ± 0.18 | 3.00 ± 0.27 | 5.73 ± 0.94 |
| Linear mean diameter, $D_v50$ (μm) | 2.10 ± 0.16 | 5.21 ± 6.87 | 5.84 ± 0.49 | 13.19 ± 1.89 |

TABLE 1-continued

Figure 5:
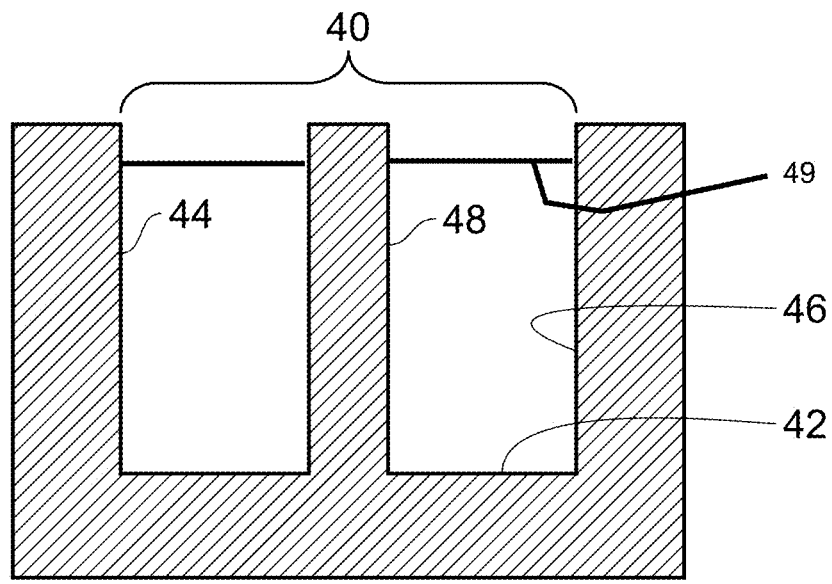
FIG. 5 shows a schematic cross sectional view of a single cavity.
Figure 6:
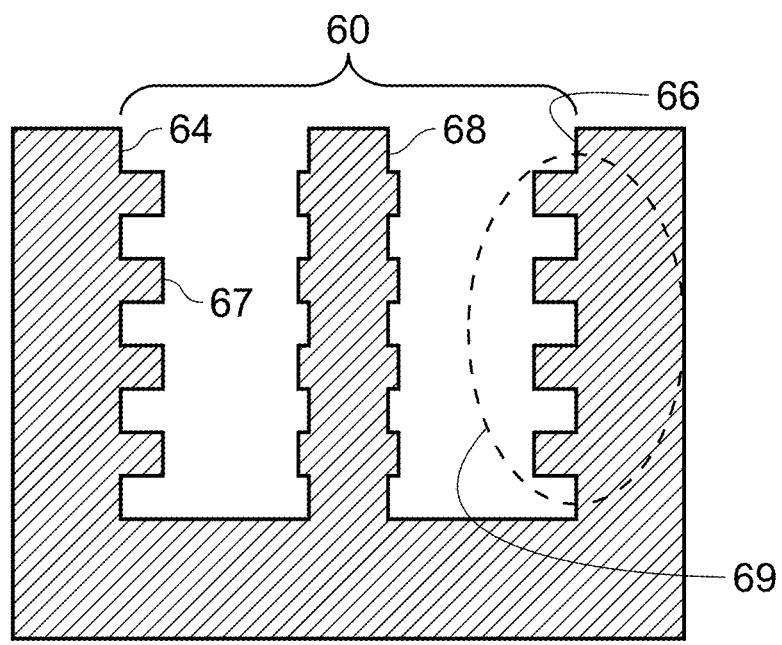
FIG. 6 shows a schematic cross sectional view of a single cavity which is a modification of the cavity shown in FIG. 5.

Derived parameters of the nebulised droplets generated by the surface acoustic waves devices and commercialised nebulisers measured using the SPRAYTEC laser diffraction system (Malvern Instruments Ltd, Malvern, UK).

| | SAW + Si superstrate with cavities | SAW (transducer only) | MEDIX MICRONEB nebuliser | MEDISANA ® nebuliser |
|---|---|---|---|---|
| Linear mean diameter, $D_v90$ (μm) | 2.50 ± 0.30 | 52.28 ± 4.06 | 11.09 ± 1.06 | 27.13 ± 6.64 |
| Surface mean diameter, $D_{32}$ (μm) | 2.16 ± 0.17 | 3.38 ± 0.82 | 5.13 ± 0.64 | 10.04 ± 1.71 |
| Volume mean diameter, $D_{43}$ (μm) | 3.45 ± 2.24 | 17.88 ± 3.47 | 6.54 ± 0.57 | 15.06 ± 2.93 |
| % Respirable Fraction (1 μm < D < 5 μm) | 96.16 ± 4.93 | 36.44 ± 6.25 | 38.38 ± 6.14 | 6.92 ± 2.89 |

In order to increase the quantity nebulised and establish the steady-state properties of the system, a syringe pump (NE-1000 Multi-Phaser™, New Era Pump Systems Inc.) was employed to regulate the amount of liquid supplied to the superstrate continuously. The pump was set to a constant flow rate of 1.0 μl/min to maintain continuous production or rapid generation of nebulised droplets.

FIGS. 4A and 4B show example frames extracted from movies on a plain superstrate (FIG. 4A) and on a superstrate having an array of cavities (FIG. 4B), illustrating the proposed hypothesis that the array of cavities prevents the generation of larger droplets.

The cavities can be formed to extend through the superstrate. This allows the cavities to be replenished with additional liquid by filling from below under capillarity. This allows the delivery of the liquid to be more robust. In this embodiment the liquid can also be used as the coupling agent.

Using a single spot and powers below 1W, the illustrated embodiment enables flow rates around 20 ul/min. The flow rate can be increased significantly by increasing actuation power (up to 5-10W) for a short period of time (<5 s).

In order to further increase the flow rate, there may be provided a plurality of locations (each having an array of cavities) at which nebulisation is carried out substantially simultaneously. In this way, the flow rate can be increased to 5 ml/min, or higher.

It is preferable to establish the nebulisation in specific areas, defined by wetting barriers. However, in the case of isotropic excitation on large arrays of cavities, the liquid may then be assembled in patches by irregularities and build up in volumes that are locally bulging above the surface of the SAW transmission surface of the superstrate. This behaviour would prevent the activity of the cavities and would result in multimodal droplet sizes, due to microdroplet ejection. Thus, it is instead preferred to provide wetting channels at the interface between the superstrate and the piezoelectric actuator. Such channels can also serve as acoustic waveguides to channel the SAWs to the nebulisation areas.

In preferred embodiments, a suitable cavity diameter is 50-200 μm. The effect of the diameter on the ability of liquid in the cavities to support capillary waves can be considered based on the driving frequency f. As explained above, the diameter D of the cavities is preferably lower than a size that would allow the generation of unwanted large droplets, thought to be the result of unwanted capillary waves.

The theoretical framework for the mechanism of large droplet suppression is not fully understood at the time of writing. The application of the progression of resonant responses from the fundamental mode upward, provided by the Lamb model, as set out in Blamey et al (2013), can be considered in which, for the sake of simplicity, the driving frequency f can be considered to be identical to $f_m$ for the fundamental mode. Whilst this is effective for low frequencies (in the kHz range or below) it is not effective for MHz range driving frequencies, for reasons which are not fully understood at the time of writing.

It is therefore more suitable here to take an empirical approach to the design of the cavities. FIG. 2(*d*) shows that nebulisation on a flat surface gives rise to a bimodal distribution. However, for the intended use of the nebulised droplets, the second peak (larger drops) is not wanted. In a preferred embodiment of the invention, cavities are formed (cylindrical holes in a superstrate to be coupled to the SAW transducer) having dimensions that prevent the capillary wave instability, in order to suppress or avoid the formation of the larger droplets. In FIG. 2(*d*), the second peak is centred on about 40 μm. Therefore the diameter of the cavities can be controlled to be less than 40 μm. This indeed will show a performance in which the larger droplets are suppressed. The inventors also report that the drop formation requires deformations of the surface that are of a scale larger than the drop size. FIG. 4 for example shows that cavities of diameter 80 μm still prevent the bigger drops. Further results (not shown) have demonstrated that cavities up to 200 um in diameter can also prevent these secondary drops.

In the schematic view shown in FIGS. 1A and 1B, the cavities 16 have a shape which is substantially hemispherical. This is intended to be illustrative. Hemispherical cavities can be used. However, more generally, cavities of other shapes can be used, e.g. cylindrical cavities, rectangular or square cylindrical cavities, circular cylindrical cavities, etc. Such cavities can have closed bottom ends. The bottoms of such cavities can be flat or rounded. In the case of etched cavities, some rounding of the bottoms is typical.

In other embodiments, the cavities may have more complex internal structures. Examples are shown in FIGS. 5-10.

FIG. 5 shows a schematic cross sectional view of a single cavity 40. The cavity has a closed bottom 42, internal walls 44, 46 and an upstanding pillar 48. Pillar 48 is supported on the closed bottom 42. In the cavity of FIG. 5, it is intended that the plan view shape of the cavity is a square, with the pillar formed at the centre. In alternative embodiments, the plan view shape of the cavity may be rectangular, other polygonal shape, round or circular. In those cases, it is possible for the pillar to be located at the geometrical centre of the shape, or located off-centre.

FIG. 6 shows a schematic cross sectional view of a single cavity 60 which is a modification of the cavity shown in FIG. 5. Here, the internal walls 64, 66 and the pillar 68 have an array of projections 67. The projections are arranged based on a periodic arrangement with the intention of interacting phononically with SAWs and affecting the transmission, distribution or other properties of the SAWs in the cavity. In this way, a phononic structure 69 is formed.

Figure 7:
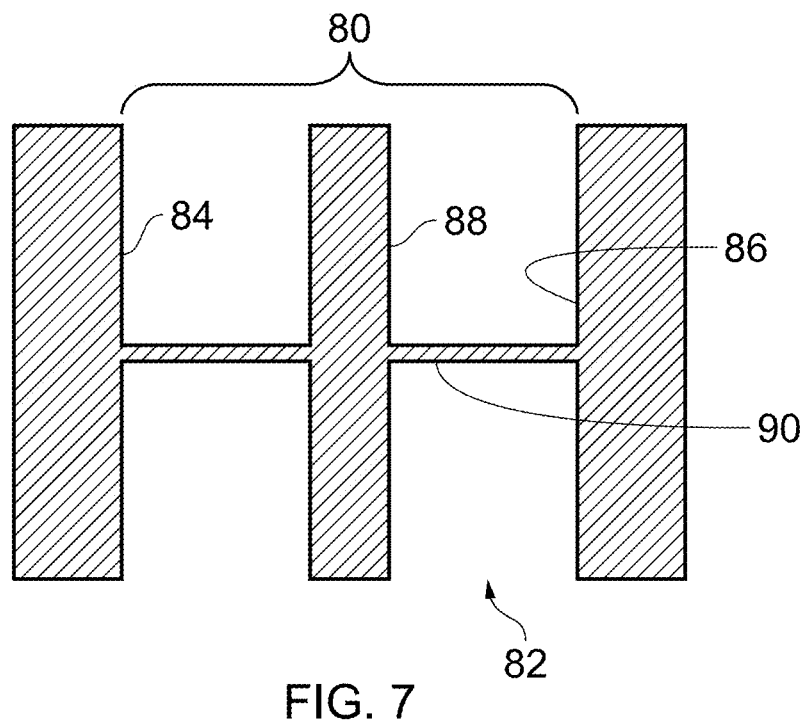
FIG. 7 shows a schematic cross sectional view of a single cavity which is another modification of the cavity shown in FIG. 5.

FIG. 7 shows a schematic cross sectional view of a single cavity 80 which is another modification of the cavity shown in FIG. 5. The cavity has an open bottom 82, internal walls 84, 86 and an upstanding pillar 88. Since there is no closed bottom to support pillar 88, it is supported by an arrangement of struts 90 extending from the internal walls 84, 86. As for the cavity of FIG. 5, it is intended that the plan view shape of the cavity is a square, with the pillar formed at the centre. In alternative embodiments, the plan view shape of the cavity may be rectangular, other polygonal shape, round or circular. In those cases, it is possible for the pillar to be located at the geometrical centre of the shape, or located off-centre.

Figure 8:
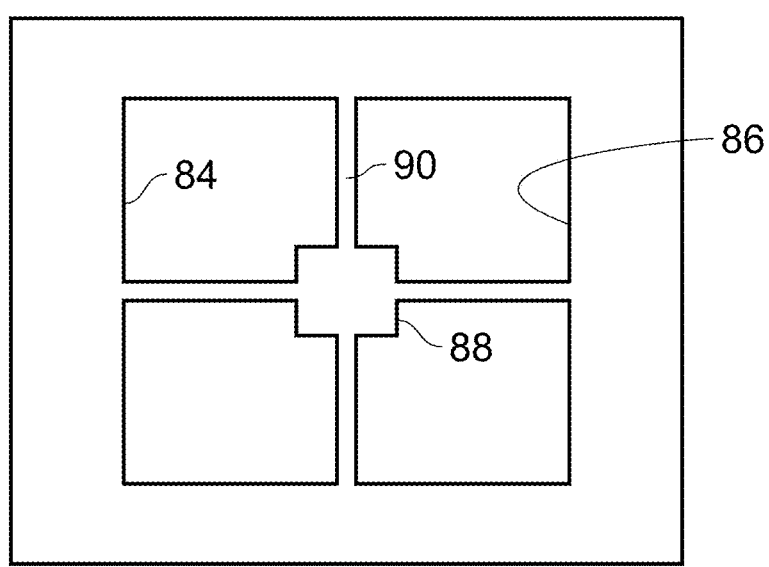
FIG. 8 shows a plan view of the cavity of FIG. 7.

FIG. 8 shows a plan view of the cavity of FIG. 7.

Figure 9:
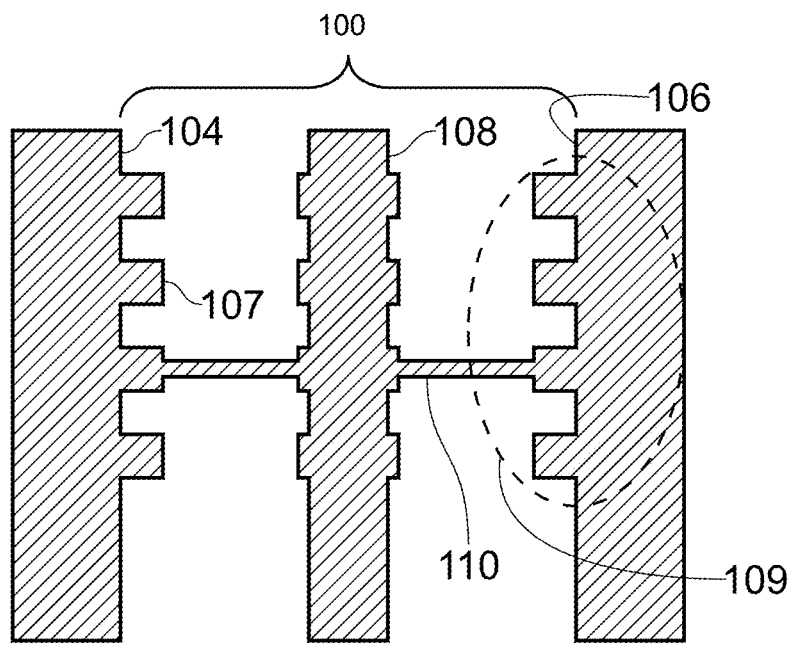
FIG. 9 shows a schematic cross sectional view of a single cavity which is a modification of the cavity shown in FIG. 8.

FIG. 9 shows a schematic cross sectional view of a single cavity 100 which is a modification of the cavity shown in FIG. 8. Here, the internal walls 104, 106 and the pillar 108 have an array of projections 107. The projections are arranged based on a periodic arrangement with the intention of interacting phononically with SAWs and affecting the transmission, distribution or other properties of the SAWs in the cavity. In this way, a phononic structure 109 is formed. Pillar 108 is supported by struts 110.

Figure 10:
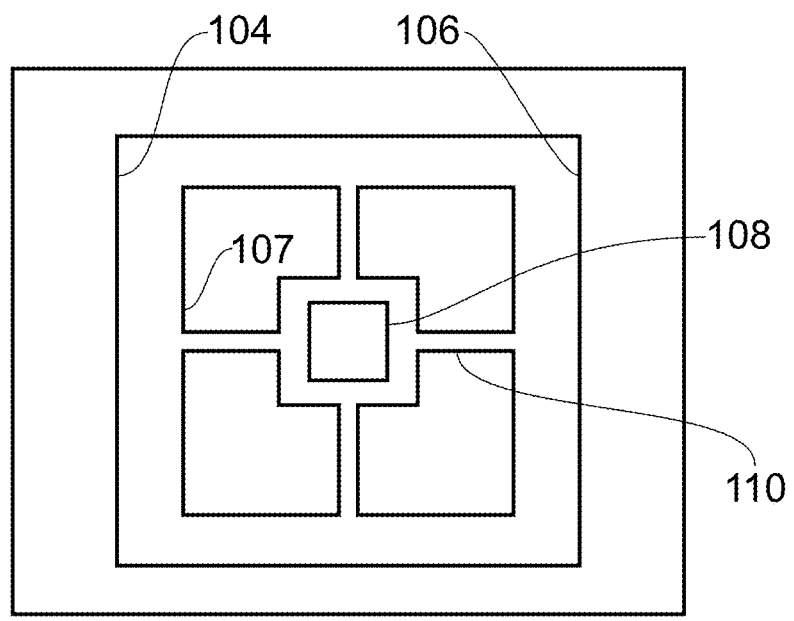
FIG. 10 shows a plan view of the cavity of FIG. 9.

FIG. 10 shows a plan view of the cavity of FIG. 9.

The use of complex cavity structures allows the interaction of the SAWs with the liquid to be controlled further. This is achieved by consideration of interaction of the fluid with the additional structures and by consideration of the interaction of the SAWs with the additional structures.

Additional investigation has been carried out to assess the effect of cavity size (also referred to herein as pore size) on aerosol droplet size. Cavities of different diameter were etched into silicon superstrates. The cavities were etched cylindrical pits with a closed bottom end, approximately 300 µm deep. Using blind cavities in this way did not allow a continuous feeding of the cavities with liquid. As a result, for each experiment, only a small volume could be nebulised at a time. For this reason, rather than carrying out an analysis of the particle size distribution based on light diffraction, as reported above, here the results are reported based on a visual observation of a small number of drops in the nebulised plumes (based on recorded microvideograph footage of the nebulised plumes).

Initially, a drop of water was placed on top of each superstrate and SAW was applied until the top layer of water disappears (either evaporate or nebulised), leaving water only in the cavities without there being liquid communication between the cavities (no water present on the surface of the superstrate between the cavities). Nebulisation from the cavities was then monitored using a fast camera (>250 kfps) fixed to a microscope, enabling the recording of images.

The largest droplets nebulised from the pores were visually assessed for their diameters.

Figure 11:
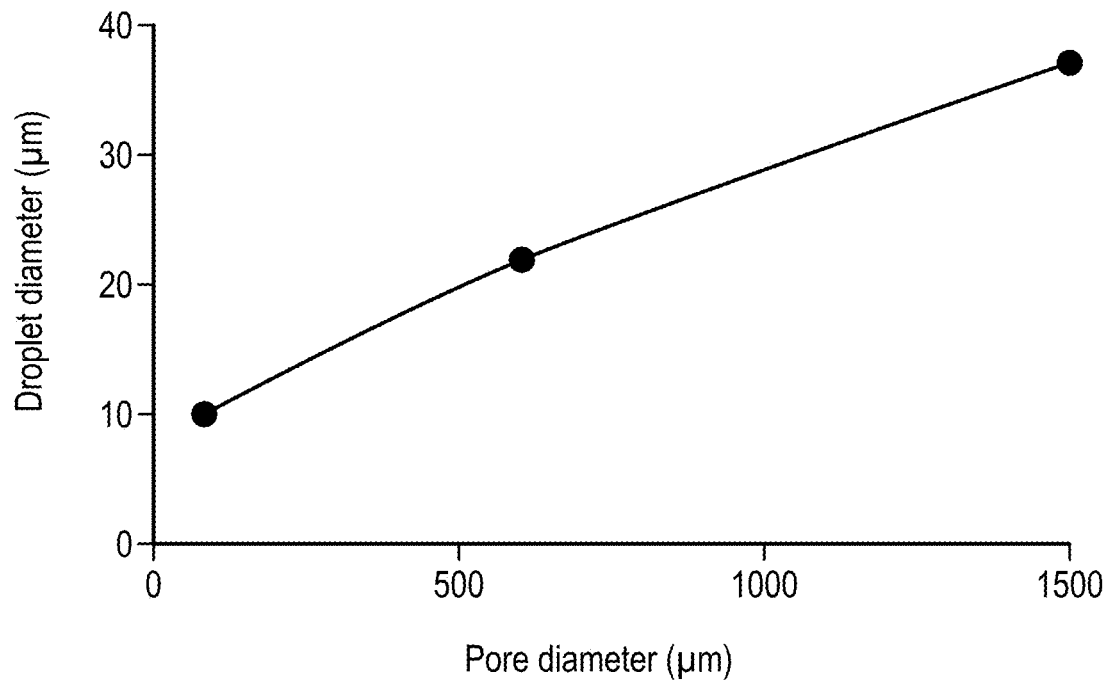
FIG. 11 shows a graph of droplet size with cavity (pore) diameter, based on an assessment of largest droplet size viewed in video footage.
Figure 12:
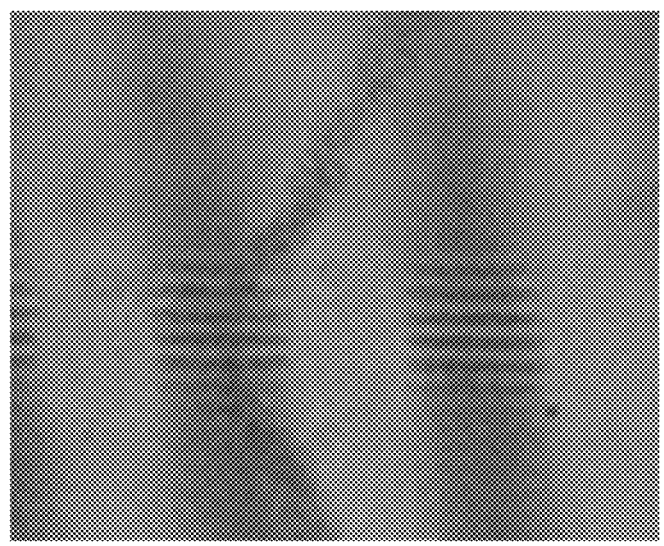
FIGS. 12-14 show images from high frame rate video footage taken using a microscope when water is nebulised from cavities of diameter 80 μm (FIG. 12), 600 μm (FIG. 13) and 1500 μm (FIG. 14).
Figure 13:
Figure 14:
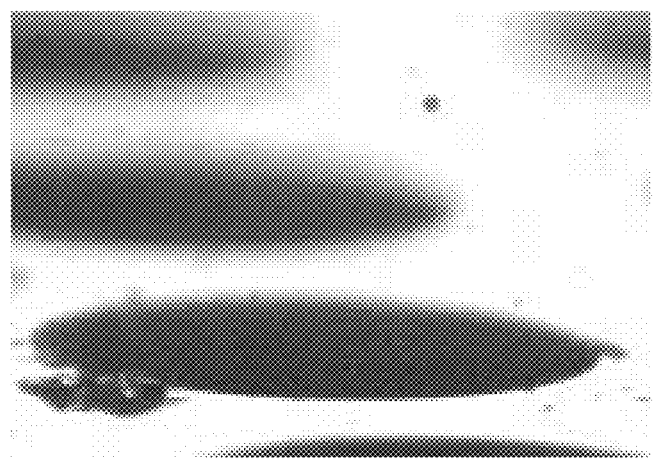

The results are shown in FIG. 11. FIGS. 12, 13 and 14 show images from the recorded footage, with FIG. 12 showing a superstrate with cavities of diameter 80 µm, FIG. 13 showing cavities of diameter 600 µm and FIG. 14 showing cavities of diameter 1500 µm. For each, the SAW was excited at 13.93 MHz and −5 dBM. The series of images was analysed and largest droplets were measured. Note that to estimate droplet size from the 80 µm cavities, the thickness of the plume were divided by the number of droplets (3 to 4 droplets) and for holes with 600 and 1500 µm diameter, single droplets were measured. For the 80 µm cavities, this was because the plume was so condensed that no single droplet could be measured.

FIG. 11 shows the variation in droplet size with cavity diameter. This shows an increase in droplet size as the cavity diameter is increased. However, the change in droplet size is not as significant as expected, but this is likely to be due to the measurement approach. Measurement of the droplet diameter distribution using light scattering in a continuous plume would demonstrate a shift in droplet size distributions, in which for small cavities (80 µm diameter), only small drops are present (<10 µm), whereas for larger cavities (1500 µm diameter), small drops are still seen, but other modes also exist to provide droplets also of large diameter (about 20-50 µm mean size). The results reported here indicate an effect attributable to the cavity diameter and correlate with the theory outlined, which is that the pinned surface layer within pores is ruled by the meniscus curvature (i.e. contact angle with pore wall). This results in a surface rigidity, suppressing capillary waves.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

All references referred to above are hereby incorporated by reference.

LIST OF NON-PATENT LITERATURE
REFERENCES

P. P. H. L. Brun, A. H. de Boer, H. W. Frijlink, and H. G. M. Heijerman, Pharm. World Sci., 2000, 22, 75-81.

J. Boe, J. H. Dennis, B. R. O'Driscoll, T. T. Bauer, M. Carone, B. Dautzenberg, P. Diot, K. Heslop, and L. Lannefors, Eur. Respir. J., 2001, 18, 228-242.

M. B. Dolovich and R. Dhand, The Lancet, 2011, 377, 1032-1045.

J. Reboud, R. Wilson, Y. Zhang, M. H. Ismail, Y. Bourquin, and J. M. Cooper, Lab. Chip, 2012, 12, 1268-1273.

J. Reboud, Y. Bourquin, R. Wilson, G. S. Pall, M. Jiwaji, A. R. Pitt, A. Graham, A. P. Waters, and J. M. Cooper, Proc. Natl. Acad. Sci., 2012, 109, 15162-15167.

A. Qi, L. Y. Yeo, and J. R. Friend, Phys. Fluids, 2008, 20, 074103.

M. Kurosawa, T. Watanabe, A. Futami, and T. Higuchi, Sens. Actuators Phys., 1995, 50, 69-74.

M. Kurosawa, A. Futami, and T. Higuchi, in Solid State Sensors and Actuators, 1997. TRANSDUCERS '97 Chicago, 1997 International Conference on, 1997, vol. 2, pp. 801-804.

M. Alvarez, J. Friend, L. Yeo, and D. Arifin, in 16th Australasian Fluid Mechanics Conference, 2007, pp. 621-624.

J. Ju, Y. Yamagata, H. Ohmori, and T. Higuchi, Sens. Actuators Phys., 2008, 145-146, 437-441.

J. Ju, Y. Yamagata, K. Inoue, and T. Higuchi, in Service Robotics and Mechatronics, eds. K. Shirase and S. Aoyagi, Springer London, 2010, pp. 309-312.

M. N. Topp, J. Aerosol Sci., 1973, 4, 17-25.

A. Qi, J. R. Friend, L. Y. Yeo, D. A. V. Morton, M. P. McIntosh, and L. Spiccia, Lab. Chip, 2009, 9, 2184.

N. Maehara, S. Ueha, and E. Mori, Rev. Sci. Instrum., 1986, 57, 2870-2876.

Wu, T. & Chang, I., 2005. Actuating and detecting of microdroplet using slanted finger interdigital transducers. Journal of Applied Physics, 98(2), 024903-7

H. Eixarch, E. Haltner-Ukomadu, C. Beisswenger and U. Bock, Drug Delivery to the Lung: Permeability and Physicochemical Characteristics of Drugs as the Basis for a Pulmonary Biopharmaceutical Classification System (pBCS), Journal of Epithelial Biology & Pharmacology, 2010, 3, 1-14.

J. Blamey, L. Y. Yeo, and J. R. Friend, Microscale Capillary Wave Turbulence Excited by High Frequency Vibration, Langmuir 2013, 29, 3835-3845.

The invention claimed is:

1. A device for the preparation of nebulised droplets, the device having:
   a surface acoustic wave (SAW) transmission surface;
   a SAW transducer adapted to generate and propagate SAWs along the SAW transmission surface; and
   an array of cavities opening at the SAW transmission surface for containing a liquid, wherein each cavity is open at an end opposite to the SAW transmission surface in fluid communication with a reservoir of the liquid to be drawn up by capillarity into the cavities to replace the liquid lost by nebulisation,
   wherein, in operation, SAWs propagating along the SAW transmission surface interact with the liquid in the cavities to produce nebulised droplets of the liquid.

2. The device according to claim 1 wherein the SAW transmission surface is a surface of a superstrate coupled to the SAW transducer and the cavities extend through a thickness of the superstrate.

3. The device according to claim 1 wherein the cavities have substantially the same shape.

4. The device according to claim 1 wherein the cavities have substantially different shapes.

5. The device according to claim 1 wherein the array of cavities are formed of substantially random shapes.

6. The device according to claim 1 wherein the cavities have substantially the same dimensions.

7. The device according to claim 1 wherein the array of cavities is an ordered array.

8. The device according to claim 1 wherein the array of cavities does not have long range order.

9. The device according to claim 1 wherein each cavity has an interior surface, said interior surface of the cavities being chemically, physically or electrically modified in order to promote the containment of the liquid in the cavities.

10. The device according to claim 1 wherein the SAW transmission surface is chemically, physically or electrically modified in order to promote the containment of the liquid in the cavities.

11. The device according to claim 1 wherein the device includes a plurality of arrays of cavities, operable to contribute to the rate of nebulisation of the liquid from the device.

12. The device according to claim 1 wherein the maximum dimension of the cavities in a direction perpendicular to the depth of the cavities is less than 500 µm.

13. A method for the preparation of nebulised droplets, including providing a device having a surface acoustic wave (SAW) transmission surface, a SAW transducer adapted to generate and propagate SAWs along the SAW transmission surface, and an array of cavities opening at the SAW transmission surface, wherein each cavity is open at an end opposite to the SAW transmission surface in fluid communication with a reservoir of a liquid to be drawn up by capillarity into the cavities to replace the liquid lost by nebulisation,
   wherein, in operation, when the SAW transmission surface is facing upwards, the liquid is contained in the cavities such that a free surface of the liquid is below a level of the SAW transmission surface, the method including the steps:
   containing the liquid in the cavities; and
   causing SAWs to propagate along the SAW transmission surface to interact with the liquid in the cavities to produce nebulised droplets of the liquid.

14. The method according to claim 13 wherein operation of the device results in a nebulised plume of the droplets of average diameter in the range 1-5 µm.

15. The method according to claim 13 wherein operation of the device results in a nebulised plume of the droplets with a respirable fraction of at least 80%.

16. The method according to claim 13 further including the step of supplying the liquid for nebulisation.

17. The method according to claim 13 wherein the SAW transmission surface is a surface of a superstrate coupled to the SAW transducer and the cavities extend through a thickness of the superstrate.

18. A method for the preparation of nebulised droplets and their delivery to a subject for therapeutic treatment, including providing a device having a surface acoustic wave (SAW) transmission surface, a SAW transducer adapted to generate and propagate SAWs along the SAW transmission surface, and an array of cavities opening at the SAW transmission surface, wherein each cavity is open at an end opposite to the SAW transmission surface in fluid communication with a reservoir of a liquid to be drawn up by capillarity into the cavities to replace the liquid lost by nebulisation,
   wherein, in operation, when the SAW transmission surface is facing upwards, the liquid is contained in the cavities such that a free surface of the liquid is below a level of the SAW transmission surface, the method including the steps:
   containing the liquid in the cavities;
   causing SAWs to propagate along the SAW transmission surface to interact with the liquid in the cavities to produce nebulised droplets of the liquid; and
   delivery of the nebulised droplets to the subject for therapeutic treatment by inhalation.

19. The method according to claim 18 wherein the SAW transmission surface is a surface of a superstrate coupled to the SAW transducer and the cavities extend through a thickness of the superstrate.

* * * * *